US009901540B2

(12) United States Patent
Mohammad et al.

(10) Patent No.: US 9,901,540 B2
(45) Date of Patent: Feb. 27, 2018

(54) COMBINATION OF ACTIVE LOADED GRANULES WITH ADDITIONAL ACTIVES

(75) Inventors: Hassan Mohammad, Cambridge (GB); Malcolm Walden, Cambridge (GB); Geoffrey Gerard Hayes, Cambridge (GB); Harjit Tamber, Cambridge (GB)

(73) Assignee: Euro-Celtique S.A., Luxembourg (LU)

( * ) Notice: Subject to any disclaimer, the term of this patent is extended or adjusted under 35 U.S.C. 154(b) by 0 days.

(21) Appl. No.: 13/697,232

(22) PCT Filed: May 10, 2011

(86) PCT No.: PCT/EP2011/057568
§ 371 (c)(1),
(2), (4) Date: Mar. 12, 2013

(87) PCT Pub. No.: WO2011/141490
PCT Pub. Date: Nov. 17, 2011

(65) Prior Publication Data
US 2013/0197021 A1    Aug. 1, 2013

(30) Foreign Application Priority Data
May 10, 2010 (EP) .................................. 10162424

(51) Int. Cl.
A61K 9/00 (2006.01)
A61K 9/16 (2006.01)
A61K 9/20 (2006.01)
A61K 31/485 (2006.01)

(52) U.S. Cl.
CPC .......... *A61K 9/0002* (2013.01); *A61K 9/1635* (2013.01); *A61K 9/1641* (2013.01); *A61K 9/1652* (2013.01); *A61K 9/205* (2013.01); *A61K 9/2027* (2013.01); *A61K 9/2031* (2013.01); *A61K 9/2095* (2013.01); *A61K 31/485* (2013.01)

(58) Field of Classification Search
None
See application file for complete search history.

(56) References Cited

U.S. PATENT DOCUMENTS

| | | | |
|---|---|---|---|
| 3,965,256 A | 6/1976 | Leslie | |
| 4,366,310 A | 12/1982 | Leslie | |
| 4,457,933 A | 7/1984 | Gordon et al. | |
| 4,647,599 A | 3/1987 | Bezzegh et al. | |
| 4,705,695 A | 11/1987 | Lehmann et al. | |
| 4,769,372 A | 9/1988 | Kreek et al. | |
| 4,785,000 A | 11/1988 | Kreek et al. | |
| 4,987,136 A | 1/1991 | Kreek et al. | |
| 5,004,613 A * | 4/1991 | Radebaugh | A61K 9/2054 424/465 |
| 5,958,452 A | 9/1999 | Oshlack et al. | |
| 6,153,644 A | 11/2000 | Owens et al. | |
| 6,277,384 B1 | 8/2001 | Kaiko et al. | |
| 6,375,957 B1 | 4/2002 | Kaiko et al. | |
| 6,419,959 B1 | 7/2002 | Walter et al. | |
| 6,475,494 B2 | 11/2002 | Kaiko et al. | |
| 6,488,961 B1 | 12/2002 | Robinson et al. | |
| 6,696,066 B2 | 2/2004 | Kaiko et al. | |
| 6,716,449 B2 * | 4/2004 | Oshlack et al. | 424/449 |
| 7,172,767 B2 | 2/2007 | Kaiko et al. | |
| 7,419,686 B2 | 9/2008 | Kaiko et al. | |
| 7,749,542 B2 | 7/2010 | Kaiko et al. | |
| 8,105,631 B2 | 1/2012 | Kaiko et al. | |
| 8,597,681 B2 | 12/2013 | Park et al. | |
| 8,673,355 B2 | 3/2014 | Kaiko et al. | |
| 8,822,487 B2 | 9/2014 | Kaiko et al. | |
| 8,846,090 B2 | 9/2014 | Brogmann et al. | |
| 8,846,091 B2 | 9/2014 | Brogmann et al. | |
| 8,932,630 B1 | 1/2015 | Kaiko et al. | |
| 8,936,808 B1 | 1/2015 | Kaiko et al. | |
| 8,969,369 B2 | 3/2015 | Caruso et al. | |
| 9,056,051 B2 | 6/2015 | Caruso et al. | |
| 9,084,729 B2 | 7/2015 | Caruso et al. | |
| 9,161,252 B2 | 10/2015 | Caruso et al. | |
| 9,161,937 B2 | 10/2015 | Caruso et al. | |
| 9,205,082 B2 | 12/2015 | Kaiko et al. | |
| 9,283,216 B2 | 3/2016 | Caruso et al. | |
| 9,283,221 B2 | 3/2016 | Caruso et al. | |
| 9,345,701 B1 | 5/2016 | Caruso et al. | |
| 9,358,230 B1 | 6/2016 | Caruso et al. | |
| 9,474,750 B2 | 10/2016 | Kaiko et al. | |
| 9,480,685 B2 | 11/2016 | Caruso et al. | |
| 9,511,066 B2 | 12/2016 | Caruso et al. | |
| 9,555,000 B2 | 1/2017 | Brogmann et al. | |
| 9,655,855 B2 | 5/2017 | Brogmann et al. | |
| 2002/0040139 A1 | 4/2002 | Billotte et al. | |
| 2003/0229111 A1 | 12/2003 | Oshlack et al. | |
| 2004/0081694 A1 | 4/2004 | Oshlack et al. | |
| 2004/0176402 A1 | 9/2004 | Oshlack et al. | |
| 2004/0242617 A1 | 12/2004 | Christoph | |
| 2005/0025802 A1 | 2/2005 | Richard et al. | |
| 2005/0032546 A1 | 2/2005 | Kehr | |
| 2005/0074493 A1 * | 4/2005 | Mehta | A61K 31/485 424/469 |
| 2005/0079221 A1 | 4/2005 | Groenewoud | |
| 2005/0095291 A1 | 5/2005 | Oshlack et al. | |
| 2005/0232987 A1 | 10/2005 | Srinivasan | |
| 2005/0245483 A1 | 11/2005 | Brogmann et al. | |
| 2005/0245556 A1 | 11/2005 | Brogmann et al. | |
| 2006/0039970 A1 | 2/2006 | Oshlack et al. | |
| 2006/0270611 A1 | 11/2006 | Dries et al. | |

(Continued)

FOREIGN PATENT DOCUMENTS

| | | |
|---|---|---|
| CA | 2766172 | 1/2001 |
| CA | 2478558 | 9/2003 |

(Continued)

OTHER PUBLICATIONS

Azamari et al., "Thermal treating as a tool for sustained release of indomethacin from Eudragit RS and RL matrices," International Journal of Pharmaceutics, 246, 171-177 (2002).

(Continued)

*Primary Examiner* — Tigabu Kassa
(74) *Attorney, Agent, or Firm* — Dechert LLP

(57) ABSTRACT

The present invention relates to prolonged release pharmaceutical dosage forms, the manufacture thereof as well as their use for administration to human being.

30 Claims, No Drawings

(56) References Cited

U.S. PATENT DOCUMENTS

| | | |
|---|---|---|
| 2007/0014732 A1 | 1/2007 | Sackler |
| 2007/0026025 A1 | 2/2007 | Mitchell |
| 2007/0048364 A1 | 3/2007 | Peng et al. |
| 2007/0141147 A1 | 6/2007 | Heil et al. |
| 2007/0259045 A1 | 11/2007 | Mannion et al. |
| 2007/0298103 A1 | 12/2007 | Hayes |
| 2008/0069875 A1 | 3/2008 | Kakiguchi et al. |
| 2008/0145429 A1 | 6/2008 | Leyendecker et al. |
| 2008/0280921 A1 | 11/2008 | Dreyer et al. |
| 2010/0151011 A1 | 6/2010 | Benke |
| 2010/0183687 A1 | 7/2010 | Cox et al. |
| 2010/0210843 A1 | 8/2010 | Hudson et al. |
| 2010/0226943 A1 | 9/2010 | Brennan et al. |
| 2010/0227876 A1 | 9/2010 | Rech |
| 2010/0331354 A1 | 12/2010 | Wermeling |
| 2011/0020451 A1 | 1/2011 | Bartholomaeus et al. |
| 2011/0077222 A1 | 3/2011 | Schaefer et al. |
| 2011/0077238 A1 | 3/2011 | Leech et al. |
| 2011/0172259 A1 | 7/2011 | Leyendecker et al. |
| 2011/0287095 A1 | 11/2011 | Park et al. |
| 2012/0108621 A1 | 5/2012 | Brogmann et al. |
| 2012/0135075 A1 | 5/2012 | Mohammad |
| 2012/0183612 A1 | 7/2012 | Brogmann et al. |
| 2012/0225901 A1 | 9/2012 | Leyendecker et al. |
| 2013/0090349 A1 | 4/2013 | Geißler et al. |
| 2013/0165467 A1 | 6/2013 | Hayes et al. |
| 2013/0178492 A1 | 7/2013 | Danagher et al. |
| 2013/0245054 A1 | 9/2013 | Prater et al. |
| 2013/0330409 A1 | 12/2013 | Mohammad |
| 2014/0031382 A1 | 1/2014 | Leyendecker et al. |
| 2015/0283091 A1 | 10/2015 | Vargas Rincon et al. |
| 2016/0095853 A1 | 4/2016 | Prater et al. |
| 2016/0296516 A1 | 10/2016 | Danagher et al. |

FOREIGN PATENT DOCUMENTS

| | | |
|---|---|---|
| CA | 2764517 | 12/2010 |
| CA | 2739751 | 11/2011 |
| CA | 2798885 | 11/2011 |
| CA | 2822553 | 6/2012 |
| CA | 2795324 | 5/2014 |
| DE | 4325465 | 2/1995 |
| DE | 10215131 A1 | 10/2003 |
| EC | SP1998-2720 | 10/1998 |
| EC | SP2000-3314 | 1/2000 |
| EC | SP2010-10416 | 8/2010 |
| EP | 0425154 A1 | 5/1991 |
| EP | 0441245 A1 | 8/1991 |
| EP | 0714661 A1 | 6/1996 |
| EP | 0880352 | 12/1998 |
| EP | 0913152 | 5/1999 |
| EP | 1557179 A1 | 7/2005 |
| EP | 1695700 | 8/2006 |
| EP | 1813276 A1 | 8/2007 |
| EP | 1961421 A1 | 8/2008 |
| EP | 2255808 | 5/2011 |
| EP | 3068397 | 9/2016 |
| FR | 2946533 | 12/2010 |
| GB | 2418854 A | 4/2006 |
| GB | 2447898 A | 10/2008 |
| JP | 2006265184 | 10/2006 |
| WO | WO 1997-016172 A1 | 5/1997 |
| WO | WO1998035679 | 8/1998 |
| WO | WO 1999-01111 A1 | 1/1999 |
| WO | WO 1999-32119 A1 | 7/1999 |
| WO | WO2001032180 | 5/2001 |
| WO | WO 2001/58447 A1 | 8/2001 |
| WO | WO 200154683 | 8/2001 |
| WO | WO 2002060385 | 8/2002 |
| WO | WO 2002/092060 | 11/2002 |
| WO | WO 2002/0100382 | 12/2002 |
| WO | WO 2003/013479 | 2/2003 |
| WO | WO 2003/013525 A1 | 2/2003 |
| WO | WO 2003/018588 | 3/2003 |
| WO | WO 2003024444 A1 | 3/2003 |
| WO | WO 2003-084504 A2 | 10/2003 |
| WO | WO 2004004683 | 1/2004 |
| WO | WO 2004091622 | 10/2004 |
| WO | WO 2004091623 | 10/2004 |
| WO | WO 2004091665 | 10/2004 |
| WO | WO 2004/098567 | 11/2004 |
| WO | WO 2005/077957 | 8/2005 |
| WO | WO 2005079760 | 9/2005 |
| WO | WO 2005/097801 | 10/2005 |
| WO | WO 2005117873 | 12/2005 |
| WO | WO 2006/043025 A1 | 4/2006 |
| WO | WO 2006038226 | 4/2006 |
| WO | WO 2006078842 | 7/2006 |
| WO | WO 2006-079550 A2 | 8/2006 |
| WO | WO 2006092064 | 9/2006 |
| WO | WO 2006/133941 | 12/2006 |
| WO | WO 2007/013047 A2 | 2/2007 |
| WO | WO 2007/039122 A2 | 4/2007 |
| WO | WO 2007/068615 A2 | 6/2007 |
| WO | WO 2008/023261 | 2/2008 |
| WO | WO 2008-049657 A2 | 5/2008 |
| WO | WO 2010032073 | 3/2010 |
| WO | WO 2010032128 | 3/2010 |
| WO | WO 2010034342 | 4/2010 |
| WO | WO 2010034344 | 4/2010 |
| WO | WO 2010068789 | 6/2010 |
| WO | WO 2010078486 | 7/2010 |
| WO | WO 2010081034 | 7/2010 |
| WO | WO 2010088911 | 8/2010 |
| WO | WO 2010096045 | 8/2010 |
| WO | WO 2010096788 | 8/2010 |
| WO | WO 2010096790 | 8/2010 |
| WO | WO 2010103039 | 9/2010 |
| WO | WO 2010105672 | 9/2010 |
| WO | WO 2010105673 | 9/2010 |
| WO | WO 2010112942 | 10/2010 |
| WO | WO 2010120232 | 10/2010 |
| WO | WO 2010121619 | 10/2010 |
| WO | WO 2010123999 | 10/2010 |
| WO | WO 2010/140007 A2 | 12/2010 |
| WO | WO 2010141505 | 12/2010 |
| WO | WO 2010142814 | 12/2010 |
| WO | WO 2010144641 | 12/2010 |
| WO | WO 2011009020 | 1/2011 |
| WO | WO 2011009602 | 1/2011 |
| WO | WO 2011009603 | 1/2011 |
| WO | WO 2011021029 | 2/2011 |
| WO | WO 2011031350 | 3/2011 |
| WO | WO 2011/141488 A2 | 11/2011 |
| WO | WO 2011/141489 A1 | 11/2011 |
| WO | WO2011141490 | 11/2011 |
| WO | WO 2012076907 | 6/2012 |
| WO | WO2012089738 | 7/2012 |
| WO | WO2013050539 | 4/2013 |
| WO | WO2015071380 | 5/2015 |

OTHER PUBLICATIONS

International Application No. PCT/GB2010/050948: International Search Report, European Patent Office, Netherlands, dated Dec. 1, 2011.

International Application No. PCT/GB2010/050948: International Preliminary Report on Patentability and Written Opinion, The International Bureau of WIPO, Geneva, Switzerland, dated Dec. 15, 2011.

International Application No. PCT/EP2011/057568: International Search Report dated Aug. 17, 2011.

International Application No. PCT/EP2011/057567: International Search Report dated Aug. 9, 2011.

International Application No. PCT/EP2011/057566: International Search Report dated Feb. 3, 2012.

Oliveto et al., "Hydromorphone-naloxone combinations in opioid-dependent humans under a naloxone novel-response discrimination procedure," Exp. and Clin. Psychopharmacology, vol. 6, No. 2, 169-178 (1998).

(56) References Cited

OTHER PUBLICATIONS

Mansour et al., "Materials for Pharmaceutical Dosage Forms: Molecular Pharmaceutics and Controlled Release Drug Delivery Aspects," Int. J. Mol. Sci. 2010, 11, 3298-3322.
Index Merck 14th, Merck & Co., USA, 2006, No. 0006362, 0004803.
Abbaspour et al, "*Thermal treating as a tool to produce plastic pellets based on Eudragit RS PO and RL PO aimed for tabletting*", European Journal of Pharmaceutics and Biopharmaceutics 2007, 67, pp. 260-267.
Alvarez, "*Sustained Release—Comparison of Acrylic & Cellulose-Based Matrix Formers for Sustained Drug Release*", Drug Delivery Technology 2006, vol. 6., No. 3.
Azarmi et al, "*Mechanistic evaluation of the effect of thermal-treating on Eudragit RS matrices*", Il farmaco 2005, 50, pp. 925-930.
Bell et al., "*The prevalence, severity, and impact of opioid-induced bowel dysfunction: results of a US and European Patient Survey (PROBE 1)*," Pain Medicine, 10(1):35-42 (2009).
Billa et al, "*Diclofenac Release from Eudragit-Containing Matrices and Effects of Thermal Treatment*", Drug Development and Industrial Pharmacy 1998, 24, pp. 45-50.
Cameron et al, "*Controlled-Release Theophylline Tablet Formulations containing Acrylic Resins, II. Combination Resin Formulations*", Drug Development and Industrial Pharmacy 1987, 13, pp. 1409-1427.
Clemens et al, "*Bowel function during pain therapy with oxycodone/naloxone prolonged release tablets in patients with advanced cancer*", International Journal of Clinical Practice 2011, 65, pp. 472-478.
Clinical Trials Study No. NCT00992576, "*Optimisation of Hydromorphone—Naloxone Ratio for the Treatment of Pain*," ClinicalTrials.gov (2009).
Coleman, "*Reducing the abuse potential of controlled substances*", Pharmaceutical Medicine 2010, 24, pp. 24-36.
Davis et al, "*Recent development in therapeutics for breakthrough pain*", Expert Review of Neuropathics 2010, 10, pp. 757-773.
Draganoiu et al, "*Development and in vitro / in vivo Evaluation of Extended Release Propranolol Tablets*", Pharm. Ind. 2006, 68, pp. 111-115.
Dumicic et al, "*The effect of water on matrix formation in sustained release tablets containing poly(ethyl acrylate, methyl methacrylate)*", J. Drug Del. Sci. Tech. 2005, 15, pp. 389-395.
European Pharmacopoeia, 4th Edition, *Directorate for the Quality of Medicines of the Council of Europe*, Council of Europe Strasbourg, 2001, ISBN:92-871-4587-3, p. 535.
Goforth et al, "*Hydromorphone-OROS formulation*", Expert Opinion on Pharmacotherapy 2010, 11, pp. 1207-1214.
Haririan et al, "*Formulation of Controlled Release Matrix Tables of Isosorbide Dinitrate*", Indian Journal of Pharmaceutical Sciences 2001, 63, pp. 24-29.
Holzer, "*New Approaches to the Treatment of Opioid-Induced Constipation*," Eur. Rev. Med. Pharmacol. Sci., 12 Suppl 1:119-27 (2008).
Jenquin et al, "*Relationship of Film Properties to Drug Release from Monolithic Films Containing Adjuvants*", Journal of Pharmaceutical Science 1992, 81, pp. 983-989.
Jost, "*Management of cancer pain: ESMO Clinical Practice Guidelines*", Annals of Oncology 2010, 21, pp. v257-v260.
Kalso et al., "*Opioids in Chronic Non-Cancer Pain: Systematic Review of Efficacy and Safety,*" Pain, 112, 372-380 (2004).
Kao et al, "*The Influence of Eudragit S-100 on the Release of Chlopheniramine Maleate from Matrix Tablets Containing Eudragit RS-PM*", The Chinese Pharmaceutical Journal 1994, 46, 257-267.
Krajacic et al, "*Matrix formation in sustained release tablets: possible mechanism of dose dumping*", International Journal of Pharmaceutics 2003, 251, pp. 67-78.
Leppert, "*Dihydrocodeine as an opioid analgesic for the treatment of moderate to severe chronic pain*", Current Drug Metabolism 2010, 11, pp. 494-506.

Leppert, "*Role of oxycodone/naloxone in cancer pain management*", Pharmacological Reports 2010, 62, 578-591.
Liu et al., "*Low-dose Oral Naloxone Reverses Opioid-Induced Constipation and Analgesia*," J. Pain Symptom Manage, 23(1):48-53 (2002).
Oxycodone / Naloxone Combination Tablet Reduces Opioid-induced Bowel Dysfunction in Patients with Chronic Severe Pain, XP00263606, [Online], Sep. 27, 2007 [retrieved on May 5, 2011] Retrieved from the internet: <URL: http://www.medicalnewstoday.com/printerfriendlynews.php?newsid=83795 >, pp. 1-2.
Palladone® retard 4, 8, 16, 24 mg, Product Label (2011).
Portenoy, "*Constipation in the Cancer Patient: Causes and Management Treatment of Constipation*" Cancer Pain, 71(2):303-311 (1987).
Rentz et al., "*Validation of the Bowel Function Index to Detect Clinically Meaningful Changes in Opioid-Induced Constipation,*" Journal of Medical Economics, 12(0):371-383 (2009).
Sadeghi et al, "*Tableting of Eudragit RS and Propranolol Hydrochloride Solid Dispersion: Effect of Particle Size, Compaction Force, and Plasticizer Addition on Drug Release*", Drug Development and Industrial Pharmacy 2004, 30, pp. 759-766.
Vela et al, "*Effect of Acrylic Resins on the Rheological and Compressibility Properties of Paracetamol: Formulation of directly compressible Matrix Systems*", Il farmaco 1995, 50, pp. 201-215.
Woods et al, "*Opioid abuse and dependence: Treatment review and future options*", Formulary 2010, 45, pp. 284-291.
Wurster et al, "*Effect of Curing on Water Diffusivities in Acrylate Free Films as Measured via Sorption Technique*", AAPS PharmSciTech 2007, 8, pp. E1-E6.
Yasser et al, "*Effect of Eudragit® RS 30D andTalc Powder on Verapamil Hydrochloride Release from Beads Coated with Drug Layered Matrices*", AMPS PharmSciTech 2007, 9, pp. 75-83.
Culpepper-Morgan et al., "Treatment of opioid-induced constipation with oral naloxone: A pilot study." Clinical Trials and Therapeutics, (1992) vol. 52(1): 90-95.
Hawkes et al., "Effect of enteric-release formulation of naloxone on intestinal transit in volunteers taking codeine"; Aliment Pharm Ther (2001) vol. 15, pp. 625-630.
I. Jurna and J. Baldauf, "Oral administration of slow-release naloxone for prevention of constipation but not analgesia following oral morphine," Der Schmerz, 7, 314-321 (1993) and translation thereof.
International Search Report and Written Opinion corresponding to International Application No. PCT/EP2014/074537 dated Feb. 10, 2015.
International Search report and Written Opinion corresponding to International Patent Application No. PCT/CA2013/000932 dated Mar. 13, 2014.
International Search Report corresponding to International Application No. PCT/CA2015/000206 dated Jul. 27, 2015.
Latasch et al., "Aufhebun einer Morphin-induzierten Obstipation durch orales Naloxon," with translation ("Oral Naloxone Antagonizes Morphine-Induced Constipation") , Anaesthesist, 46, 191-194 (1997).
Meissner et al., "A randomized controlled trial with prolonged-release oral oxycodone and naloxone to prevent and reverse opioid-induced constipation," Eur. J. Pain, vol. 13, pp. 56-64 (2009).
Meissner et al., "Oral naloxone reverses opioid-associated constipation", Pain, vol. 84, pp. 105-109 (2000).
Nagata, "Advantages to HPMC Capsules: A New Generation's", Drug Development and Delivery, vol. 2, No. 2, Mar./Apr. 2002, pp. 1-8.
Sykes "An investigation of the ability of oral naloxone to correct opioid-related constipation in patients with advanced cancer," Palliative Medicine (1996), 10:134-144.
Sykes "Oral naloxone in opioid-associated constipation," Lancet (1991) vol. 337 p. 1475.
Taiwan Application No. 100116427: Office Action and Search Report dated Mar. 12, 2013.

\* cited by examiner

US 9,901,540 B2

COMBINATION OF ACTIVE LOADED GRANULES WITH ADDITIONAL ACTIVES

CROSS REFERENCE TO RELATED APPLICATIONS

This application is a national stage entry of International Application No. PCT/EP2011/057568, filed May 10, 2011, and claims priority under 35 U.S.C. § 119(a)-(d) and 365(b) of European Patent Application No. EP 10162424.5, filed 10 May 2010, the contents of all of which are incorporated herein in their entireties by reference thereto.

FIELD OF THE INVENTION

The present invention relates to prolonged release pharmaceutical dosage forms, the manufacture thereof as well as their use for administration to human beings.

BACKGROUND OF THE INVENTION

Prolonged release pharmaceutical dosage forms represent an important tool in a medical practioner's armoury for treating diseases. One of the general benefits generally attributed to prolonged release pharmaceutical dosage forms versus immediate release pharmaceutical dosage forms includes increased patient compliance as a consequence of reduced administration frequency.

Various technologies are available for obtaining prolonged release dosage forms. Prolonged release properties may be conveyed by so-called prolonged release matrix systems, prolonged release coatings, osmotic dosage forms, multi-layered dosage forms, etc.

When developing a prolonged release formulation, it is generally necessary to choose the formulation technology with respect to the physico-chemical and physiological properties of the pharmaceutically active agent(s) in question. This means a substantial amount of work to the formulation specialist.

There is thus a continuing interest in further developments which make manufacturing of prolonged release dosage forms more straightforward.

SUMMARY OF THE INVENTION

It is an objective of the present invention to provide prolonged release pharmaceutical dosage forms and methods of manufacture thereof.

These and other objectives, as they will become apparent from the ensuing descriptions, are attained by the subject matter of the independent claims. Some of the preferred embodiments are referred to by the dependent claims.

To some extent, the present invention is based on the finding that it is possible to produce granules containing a prolonged release material and at least one first pharmaceutically active agent and to then compress these granules with at least one additional pharmaceutically active agent. It seems that a prolonged release matrix is obtained at least upon compression which conveys prolonged release properties on the prolonged release pharmaceutical composition. As the active agent loaded-granules may be used with a variety of different pharmaceutically active agents, this approach greatly facilitates the manufacture of prolonged release dosage forms having at least two pharmaceutically active agents.

In one aspect, the present invention thus relates to a method of manufacturing an oral prolonged release pharmaceutical composition comprising at least the steps of:
  a) producing granules comprising at least one prolonged release material and at least one first pharmaceutically active agent;
  b) optionally selecting granules of step a) of substantially uniform size;
  c) blending said granules of step a) or step b) with at least one additional pharmaceutically active agent;
  d) compressing said granules of step c) to obtain an oral prolonged release pharmaceutical composition in the form of a tablet.

In one embodiment, granules of step a) are manufactured by fluidised bed or wet granulation. In another embodiment, the granules are obtained by extrusion In one embodiment, the granules are optionally screened in order to select granules of substantially uniform size. For example, granules may be selected to have granule mean sizes in the range of about 100 μm to about 2 mm. Before screening, the granules may also be milled.

In one embodiment, an additional curing step may be included after step d).

In one embodiment the at least one first pharmaceutically active agent is an opioid agonist and the at least one additional pharmaceutically active agent is an opioid antagonist. Oxycodone hydrochloride, hydrocodone hydrochloride and hydromorphone hydrochloride are particularly preferred as opioid agonists and naloxone hydrochloride is preferably used as an opioid antagonist.

Another aspect of the present invention relates to prolonged release pharmaceutical compositions as they are obtainable by methods in accordance with the invention.

Such dosage forms may be alcohol resistant as described hereinafter. They may also provide good mechanical tamper resistance.

DETAILED DESCRIPTION OF THE INVENTION

The present invention as illustratively described in the following may suitably be practiced in the absence of any element or elements, limitation or limitations, not specifically disclosed herein.

The present invention will be described with respect to particular embodiments and with reference to certain figures but the invention is not limited thereto but only by the claims. Terms as set forth hereinafter are generally to be understood in their common sense unless indicated otherwise.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group which preferably consists only of these embodiments.

Where an indefinite or definite article is used when referring to a singular noun, e.g. "a", "an" or "the", this includes a plural of that noun unless something else is specifically stated.

In the context of the present invention the terms "about" or "approximately" denote an interval of accuracy that the person skilled in the art will understand to still ensure the technical effect of the feature in question. The term typically indicates deviation from the indicated numerical value of ±10%, and preferably of ±5%.

The term "in vitro release" and its grammatical variations as well as similar expression refers to the release rate by which a pharmaceutically active agent, e.g. hydromorphone HCl is released from the pharmaceutical composition when the in vitro release rate is tested by the paddle method according to the European Pharmacopeia as described in as described in the Ph. Eur. 2.9.3 6$^{th}$ edition. The paddle speed is set at 100 rpm in simulated gastric fluid (SGF) dissolution medium with pH 1.2. Aliquots of the dissolution media are withdrawn at the respective time points and analysed by HPLC with a C18 column, eluted with 30 mM phosphate buffer in acetonitrile (70:70; pH 2.9) with a flow rate of 1.0 ml/min and detected at 220 nm. It is specifically indicated if in the context of the present invention in vitro release rates are determined using a different test method (such as SGF with 40% (v/v) of ethanol).

The term "Simulated Gastric Fluid, pH 1.2" refers to 0.1 N HCl, pH 1.2.

In the context of the present invention, the terms "immediate release" or "conventional release" refer to pharmaceutical compositions showing a release of the active substance(s) which is not deliberately modified by a special formulation design and/or manufacturing methods. For oral dosage forms this means that the dissolution profile of the active substance(s) depends essentially on its (theirs) intrinsic properties. Typically, the terms "immediate release" or "conventional release" refer to pharmaceutical compositions which release in vitro >75% (by weight) of the pharmaceutically active agent(s) at 45 min.

In the context of the present, the terms "prolonged release" and "controlled release" are used interchangeably and refer to pharmaceutical compositions showing a slower release of the active agent(s) than that of a conventional release pharmaceutical composition administered by the same route. Prolonged or controlled release is achieved by a special formulation design and/or manufacturing method. Typically, the terms "prolonged release" and "controlled release" refer to pharmaceutical compositions which release in vitro ≤75% (by weight) of the pharmaceutically active agent at 45 min.

Prolonged release properties may be obtained by different means such as by a coating which is then designated as a prolonged release coating, a matrix which is then designated as a prolonged release matrix or e.g. by an osmotic structure of the pharmaceutical composition.

In order to obtain "prolonged or controlled release" properties, one typically uses materials which are known to prolong the release from a dosage form comprising e.g. a prolonged release matrix and/or prolonged release coating. Typical examples of such "prolonged or controlled release materials" are hydrophobic polymers such as ethyl cellulose, hydrophilic polymers such as hydroxypropyl cellulose and the like. The nature of the "prolonged or controlled release material" may depend on whether the release properties are attained by a "prolonged release matrix" or a "prolonged release coating". The term "prolonged release materials" thus describes both types of materials. The term "prolonged release matrix material" indicates that a material is used for obtaining a prolonged release matrix. Likewise, the term "prolonged release coating material" indicate that a material is used for obtaining a prolonged release coating.

The terms "prolonged release matrix formulation" or "controlled release matrix formulation" refer to a pharmaceutical composition including at least one prolonged release material or controlled release material, and at least one pharmaceutically active agent. The terms "prolonged release material" and "controlled release material" can be used interchangeably. In a "prolonged release matrix formulation" or "controlled release matrix formulation", the "prolonged release material" or "controlled release material" are combined with the pharmaceutically active agent(s) to form a mixture from which the pharmaceutically active agent is released over prolonged periods of time, such as e.g. 8, 10, 12, 14, 16, 18, 20, 22 or 24 hours.

It is to be understood that a material will be considered to act as prolonged or controlled release material if the dissolution profile of the pharmaceutically active agent(s) is slowed down compared to an immediate or conventional release formulation. If a prolonged or controlled release material can be used for manufacturing a prolonged or controlled release matrix, it will be considered as a prolonged or controlled release matrix material.

Pharmaceutically acceptable excipients which are used to adjust an already prolonged or controlled release to a specific profile are not necessarily considered to be prolonged or controlled release materials.

It is to be understood that a prolonged release matrix or a controlled release matrix does not necessarily consist only of the pharmaceutically active agent(s) and the prolonged or controlled release material. The prolonged or controlled release matrix may comprise in addition pharmaceutically acceptable excipients such as fillers, lubricants, glidants, etc.

The terms "prolonged release coating formulation" or "controlled release coating formulation" refer to a pharmaceutical composition including at least one prolonged release material or controlled release material, and at least one pharmaceutically active agent. The terms "prolonged release material" and "controlled release material" can be used interchangeably. In a "prolonged release coating formulation" or "controlled release coating formulation", the "prolonged release material" or "controlled release material" are disposed on the pharmaceutically active agents to form a diffusion barrier. Other than in prolonged release matrix formulation, the actives are not intimately mixed with the prolonged release material and the prolonged release coating does not form a three dimensional structure within which the actives are distributed. As the term implies, the prolonged release material forms a layer above the actives. The pharmaceutically active agent is released from a prolonged release coating formulation over prolonged periods of time, such as e.g. 8, 10, 12, 14, 16, 18, 20, 22 or 24 hours.

It is to be understood that a material will be considered to act as prolonged or controlled release material if the dissolution profile of the pharmaceutically active agent(s) is slowed down compared to an immediate or conventional release formulation. If a prolonged or controlled release material can be used for manufacturing a prolonged or controlled release coating, it will be considered as a prolonged or controlled release coating material.

Pharmaceutically acceptable excipients which are used to adjust an already prolonged or controlled release to a specific profile are not necessarily considered to be prolonged or controlled release materials.

When it is mentioned that a prolonged release coating is disposed on pharmaceutically active agents, this is not to be construed as meaning that such a coating will necessarily be directly layered on such active pharmaceutically agents. Of course, if pharmaceutically active agents are layered on a carries such as nu-pareil beads, the coating may be disposed directly thereon. However, the pharmaceutically active agents may also be first embedded in a polymer layer or e.g.

a prolonged release matrix. Subsequently the prolonged release coating may be disposed on e.g. granules which comprise a prolonged release matrix or on tablets which are made from such granules by compression for example.

A pharmaceutical composition with a controlled or prolonged release coating may be obtained by combining the pharmaceutically active agents with a carries such as non-pareil beads and disposing a prolonged release coating on said combinations. Such coating may be made from polymers such cellulose ethers with ethyl cellulose being preferred, acrylic resins, other polymers and mixtures thereof. Such controlled or prolonged release coatings may comprise additional excipients such as pore-formers, binders and the like.

It is further to be understood, that the term "prolonged release matrix formulation" or "controlled release matrix formulation" does not exclude pharmaceutical compositions with a prolonged or controlled release matrix and an additional prolonged or controlled release coating being disposed on the matrix. Likewise the term "prolonged release coating formulation" or "controlled release coating formulation" does not exclude pharmaceutical compositions with a prolonged or controlled release coating which is disposed on prolonged release matrix or a controlled release matrix.

The terms "prolonged release dosage form" and "controlled release dosage form" can be used interchangeably and refer to the administration form of a pharmaceutical composition of the present invention comprising the at least one pharmaceutically active agent in prolonged release form as e.g. in form of a "prolonged release matrix formulation", in the form of a "prolonged release coating formulation, combinations thereof or in other prolonged release formulations such as osmotic formulations. The terms "prolonged release matrix formulation" and "prolonged release dosage form" can be used interchangeably if the prolonged release dosage form consists essentially of the prolonged release matrix formulation. This means that a prolonged release dosage form can comprise in addition to the prolonged release matrix e.g. cosmetic coatings and pharmaceutically acceptable excipients such fillers, lubricants, etc.

For some embodiments, the term "prolonged release matrix dosage form" may indicate that the dosage form comprises a prolonged release matrix as the sole structure being responsible for prolonging the release. This, however, does not exclude that the dosage form may comprise an immediate release portion as described hereinafter.

For some embodiments, the term "prolonged release coating dosage form" may indicate that the dosage form comprises a prolonged release coating as the sole structure being responsible for prolonging the release. This, however, does not exclude that the dosage form may comprise an immediate release portion as described hereinafter.

The release rates indicated always refer to the formulation such as a monolithic tablet or multi-particulates. The release rates will be chosen such that a pharmaceutical composition can be administered e.g. on a twice a day or once a day basis, i.e. every 12 hours or every 24 hours. Typically, the release will occur by diffusion through the prolonged or controlled release matrix and/or coating, erosion of the prolonged or controlled matrix and/or coating or combinations thereof.

The term "alcohol resistance" and its grammatical variations refer to the property of pharmaceutical compositions of the invention to release about the same or less amount of the pharmaceutically active agent(s) in vitro, the in vitro release rate being tested in 500 ml or 1000 ml of Simulated Gastric Fluid, pH 1.2 with up to 40% (v/v) ethanol using the Ph. Eur. Paddle method at 100 rpm at 37° C. compared to the in vitro release rate being tested in 500 or 1000 ml of Simulated Gastric Fluid, pH 1.2 with up to 0% (v/v) ethanol using the Ph. Eur. Paddle method at 100 rpm at 37° C. The amount of dissolution liquid may depend on the amount of active agent tested. For example, pharmaceutical compositions comprising up to 8 mg hydromorphone HCl may be tested in 500 ml dissolution liquid while higher dosage strengths may be tested in 1000 ml dissolution liquid.

Resistance to alcohol extraction can e.g. be tested by subjecting the formulation to Simulated Gastric Fluid (SGF), pH 1.2 with 40% ethanol. A typical manner in order to obtain "500 ml of Simulated Gastric Fluid (SGF), pH 1.2 with 40% ethanol" is by mixing 600 ml of SGF with 420 ml of 95% ethanol/water (which provides 400 ml of 100% ethanol) and taking 500 ml of the mixture. The effect of the additional 20 ml of water from the 95% ethanol will be minimal in the percentages of SGF and ethanol in the 500 ml mixture.

A typical manner in order to obtain 500 ml of Simulated Gastric Fluid (SGF), pH 1.2 with 40% ethanol" is by mixing 600 ml of SGF with 420 ml of 95% ethanol/water (which provides 400 ml of 100% ethanol) and taking 500 ml of the mixture. The effect of the additional 20 ml of water from the 95% ethanol will be minimal in the percentages of SGF and ethanol in the final 500 ml mixture.

In certain embodiments, the present invention is directed to a prolonged release pharmaceutical composition comprising at least two pharmaceutically active agents and at least one prolonged release material being combined to form a prolonged release matrix; wherein the ratio of the amount of the at least one first pharmaceutically active agent released after 0.5, 1 or 2 hours of in vitro dissolution of the dosage form in 500 or 1000 ml of Simulated Gastric Fluid, pH 1.2 with up to 40% ethanol using the Ph. Eur. paddle method at 100 rpm at 37 C compared to the amount of the at least one first pharmaceutically active agent released after 0.5, 1 or 2 hours in vitro dissolution of the dosage form in 500 or 1000 ml of Simulated Gastric Fluid, pH 1.2 with 0% ethanol using the Ph. Eur. paddle method at 100 rpm at 37° C. is about 2:1 or less, about 1.5:1 or less, about 1:1 or less, about 1:1.2 or less, about 1:1.4 or less, about 1:1.6 or less, about 1:1.8 or less, about 1:2 or less, about 1:2.5 or less about 1:3 or less or about 1:5 or less, and wherein the ratio of the amount of the at least one additional pharmaceutically active agent released after 1 hour of in vitro dissolution of the dosage form in 500 or 1000 ml of Simulated Gastric Fluid, pH 1.2 with up to 40% ethanol using the Ph. Eur. paddle method at 100 rpm at 37° C. compared to the amount of the at least one additional pharmaceutically active agent released after 0.5, 1 or 2 hours in vitro dissolution of the dosage form in 500 or 1000 ml of Simulated Gastric Fluid, pH 1.2 with 0% ethanol using the Ph. Eur. paddle method at 100 rpm at 37° C. is about 2:1 or less, about 1.5:1 or less, about 1:1 or less, about 1:1.2 or less, about 1:1.4 or less, about 1:1.6 or less, about 1:1.8 or less, about 1:2 or less, about 1:2.5 or less about 1:3 or less or about 1:5 or less. Preferably, the ratio is about 1:1 or less such as 1:1.5 or 1:2.

In certain embodiments of the invention, which can be preferred, the at least one first pharmaceutically active agent is an opioid agonist and the at least one additional pharmaceutically active agent in an opioid antagonist.

For purposes of the present invention, the term "opioid" is interchangeable with the term "opioid analgesic" and includes one agonist or a combination of more than one opioid agonist, and also includes the use of a mixed agonist-antagonist; a partial agonist and combinations of an opioid agonist and an opioid antagonist, wherein the combination provides an analgesic effect, stereoisomers thereof; an ether or ester thereof; or a mixture of any of the foregoing. With respect to certain embodiments of the present invention, the term "opioid agonist" is interchangeable with the term "opioid analgesic" and includes one agonist or a combination of more than one opioid agonist, and also includes the use of a mixed agonist-antagonist; a partial agonist, stereoisomers thereof, an ether or ester thereof, or a mixture of any of the foregoing.

The present invention disclosed herein is meant to encompass the use of any pharmaceutically acceptable salt of an opioid agonist, a mixed opioid agonist-antagonist or of an opioid antagonist. The term "opioid salt" refers to a pharmaceutically acceptable salt of the opioid, of the mixed opioid agonist-antagonist or of the opioid antagonist. Any embodiment of the invention referring to opioid is also meant to refer to opioid salt.

Pharmaceutically acceptable salts include, but are not limited to, inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, asparginate, glutamate and the like, and metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like.

The opioids used according to the present invention may contain one or more asymmetric centers and may give rise to enantiomers, diastereomers, or other stereoisomeric forms. The present invention is also meant to encompass the use of all such possible forms as well as their racemic and resolved forms and compositions thereof. When the compounds described herein contain olefinic double bonds or other centers of geometric asymmetry, it is intended to include both E and Z geometric isomers. All tautomers are intended to be encompassed by the present invention as well.

As used herein, the term "stereoisomers" is a general term for all isomers of individual molecules that differ only in the orientation of their atoms is space. It includes enantiomers and isomers of compounds with more than one chiral center that are not mirror images of one another (diastereomers).

The term "chiral center" refers to a carbon atom to which four different groups are attached.

The term "enantiomer" or "enantiomeric" refers to a molecule that is non-superimposable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule.

Opioid agonists useful in the present invention include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl and derivatives, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, noripanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, tramadol, pharmaceutically acceptable salts, hydrates and solvates thereof, mixtures of any of the foregoing, and the like.

Opioid antagonists useful in combination with opioid agonists as described above are e.g. naloxone, naltrexone and nalmephene or pharmaceutically acceptable salts, hydrates and solvates thereof, mixtures of any of the foregoing, and the like.

In certain embodiments, the opioid analgesic is selected from codeine, morphine, oxycodone, hydrocodone, hydromorphone, tramadol or oxymorphone or pharmaceutically acceptable salts, hydrates and solvates thereof, mixtures of any of the foregoing, and the like. The opioid antagonist, if present, may be naloxone or pharmaceutically acceptable salts, hydrates and solvates thereof, mixtures of any of the foregoing, and the like. The use of the hydrochloride salts of both the opioid analgesic and the opioid antagonist can be preferred.

If in the following reference is made to a pharmaceutically active agent such as hydromorphone, this always also includes the reference to a pharmaceutically acceptable salt of the free base of this pharmaceutically active agent unless it is specifically indicated that the reference to the pharmaceutically active agent, such as use of the term "hydromorphone" should only refer to the free base.

In certain embodiments, the opioid analgesic is oxycodone, hydromorphone or oxymorphone or a salt thereof such as e.g. the hydrochloride. The dosage form comprises from about 5 mg to about 500 mg oxycodone hydrochloride, from about 1 mg to about 100 mg hydromorphone hydrochloride or from about 5 mg to about 500 mg oxymorphone hydrochloride. If other salts, derivatives or forms are used, equimolar amounts of any other pharmaceutically acceptable salt or derivative or form including but not limited to hydrates and solvates or the free base may be used. The dosage form comprises e.g. 5 mg, 7.5 mg, 10 mg, 15 mg, 20 mg, 30 mg, 40 mg, 45 mg, 60 mg, or 80 mg, 90 mg, 120 mg or 160 mg oxycodone hydrochloride or equimolar amounts of any other pharmaceutically acceptable salt, derivative or form including but not limited to hydrates and solvates or of the free base. The dosage form comprises e.g. 5 mg, 7.5 mg, 10 mg, 15 mg, 20 mg, 30, mg, 40 mg, 45 mg, 60 mg, or 80 mg, 90 mg, 120 mg or 160 mg oxymorphone hydrochloride or equimolar amounts of any other pharmaceutically acceptable salt, derivative or form including but not limited to hydrates and solvates or of the free base. The dosage form comprises e.g. 2 mg, 4 mg, 8 mg, 12 mg, 16 mg, 24 mg, 32 mg, 48 mg or 64 mg hydromorphone hydrochloride or equimolar amounts of any other pharmaceutically acceptable salt, derivative or form including but not limited to hydrates and solvates or of the free base.

If the dosage form in addition to oxycodone hydrochloride comprises e.g. naloxone hydrochloride, this may be present in amounts of e.g. 2.5 mg, 5 mg, 10 mg, 20 mg, 40 mg or 80 mg naloxone hydrochloride or equimolar amounts of any other pharmaceutically acceptable salt, derivative or form including but not limited to hydrates and solvates or of the free base.

If the dosage form in addition to hydromorphone hydrochloride comprises e.g. naloxone hydrochloride, this may be present in amounts of e.g. 1 mg, 2 mg, 4 mg, 8 mg, 12 mg, 16 mg, 24 mg, 32 mg, 48 mg, 64 mg, 96 mg, 128 or 256 mg naloxone hydrochloride or equimolar amounts of any other pharmaceutically acceptable salt, derivative or form including but not limited to hydrates and solvates or of the free base.

If specific amounts of oxycodone hydrochloride, hydromorphone hydrochloride or naloxone hydrochloride are mentioned above, this refers to the anhydrous forms thereof.

In certain embodiments e.g. a combination of oxycodone HCl and naloxone HCl in a ratio of 2:1 by weight is used.

In other embodiments, e.g. a combination of hydromorphone HCl and naloxone HCl in a ratio of 2:1, 1:1, 1:2, 1:3 or 1:4 by weight is used.

In a preferred embodiment, the pharmaceutical compositions in accordance with the invention may comprise an opioid agonist and antagonist as sole pharmaceutically active agents.

In another preferred embodiment, the pharmaceutical compositions in accordance with the invention may comprise hydromorphone HCl and naloxone HCl as sole pharmaceutically active agents.

In another embodiments, the present invention is directed to a prolonged release pharmaceutical compositions comprising at least two pharmaceutically active agents and at least one prolonged release material being combined to form a prolonged release matrix; wherein the ratio of the amount of the at least one first pharmaceutically active agent released after 0.5, 1 or 2 hours of in vitro dissolution of the dosage form in 500 or 1000 ml of Simulated Gastric Fluid, pH 1.2 with up to 40% ethanol using the Ph. Eur. paddle method at 100 rpm at 37° C. compared to the amount of the at least one first pharmaceutically active agent released after 0.5, 1 or 2 hours in vitro dissolution of the dosage form in 500 or 1000 ml of Simulated Gastric Fluid, pH 1.2 with 0% ethanol using the Ph. Eur. paddle method at 100 rpm at 37° C. is about 2:1 or less, about 1.5:1 or less, about 1:1 or less, about 1:1.2 or less, about 1:1.4 or less, about 1:1.6 or less, about 1:1.8 or less, about 1:2 or less, about 1:2.5 or less about 1:3 or less or about 1:5 or less; wherein the ratio of the amount of the at least one additional pharmaceutically active agent released after 0.5, 1 for 2 hours of in vitro dissolution of the dosage form in 500 or 1000 ml of Simulated Gastric Fluid pH 1.2 with up to 40% ethanol using the Ph. Eur. paddle method at 100 rpm at 37° C. compared to the amount of the at least one additional second pharmaceutically active agent released after 0.5, 1 or 2 hours in vitro dissolution of the dosage form in 500 or 1000 ml of Simulated Gastric Fluid pH 1.2 with 0% ethanol using the Ph. Eur. paddle method at 100 rpm at 37° C. is about 2:1 or less, about 1:5:1 or less, about 1:1 or less, about 1:1.2 or less, about 1:1.4 or less, about 1:1.6 or less, about 1:1.8 or less, about 1:2 or less, about 1:2.5 or less about 1:3 or less or about 1:5 or less; wherein the first pharmaceutically active agent is an opioid agonist and the second pharmaceutically active agent is an opioid antagonist. Preferably, the ratio is about 1:1 or less such as 1:1.5 or 1:2. Preferably, the opioid agonist is oxycodone HCl or hydromorphone HCl and the opioid antagonist is naloxone HCl. The prolonged release pharmaceutical composition may comprise these actives in the above indicated amounts and ratios. These prolonged release pharmaceutical compositions may be obtained by the methods described hereinafter.

In some embodiments, the present invention is directed to a prolonged release pharmaceutical composition comprising at least two pharmaceutically active agents and at least one prolonged release material being combined to form a prolonged release matrix; wherein the amount of the at least two pharmaceutically active agents released in vitro in 500 or 1000 ml of Simulated Gastric Fluid pH 1.2 using the Ph. Eur. paddle method at 100 rpm at 37° C. is:

at 0.5 h: 10 to 50% by weight of the pharmaceutically active agents,
at 1 h: 20 to 60% by weight of the pharmaceutically active agents,
at 2 h: 30 to 70% by weight of the pharmaceutically active agents,
at 3 h: 40 to 80% by weight of the pharmaceutically active agents,
at 4 h: 50 to 90% by weight of the pharmaceutically active agents,
at 5 h: 55 to 95% by weight of the pharmaceutically active agents,
at 6 h: 60 to 100% by weight of the pharmaceutically active agents,
at 8 h: 70 to 100% by weight of the pharmaceutically active agents,
at 12 h: 80 to 100% by weight of the pharmaceutically active agents.

These amounts refer to each of the at least two pharmaceutically active agents.

The pharmaceutically active agents may be an opioid agonist with oxycodone HCl or hydromorphone HCl being preferred and an opioid antagonist with naloxone HCl being preferred. The prolonged release pharmaceutical composition may comprise these actives in the above indicated amounts and ratios. The composition may be alcohol resistant as described above. These prolonged release pharmaceutical compositions may be obtained by the methods described hereinafter.

Preferably, the amount of the pharmaceutically active agents released in vitro in 500 or 1000 ml of Simulated Gastric Fluid pH 1.2 using the Ph. Eur. paddle method at 100 rpm at 37° C. is:

at 0.5 h: 20 to 40% by weight of the pharmaceutically active agents,
at 1 h: 25 to 45% by weight of the pharmaceutically active agents,
at 2 h: 35 to 55% by weight of the pharmaceutically active agents,
at 3 h: 45 to 65% by weight of the pharmaceutically active agents,
at 4 h: 55 to 75% by weight of the pharmaceutically active agents,
at 5 h: 60 to 80% by weight of the pharmaceutically active agents,
at 6 h: 65 to 85% by weight of the pharmaceutically active agents,
at 8 h: 75 to 95% by weight of the pharmaceutically active agents,
at 12 h: 85 to 100% by weight of the pharmaceutically active agents.

These amounts refer to each of the at least two pharmaceutically active agents.

The pharmaceutically active agents may be an opioid agonist with oxycodone HCl or hydromorphone HCl being preferred and an opioid antagonist with naloxone HCl being preferred. The prolonged release pharmaceutical composition may comprise these actives in the above indicated amounts and ratios. The composition may be alcohol resistant as described above. These prolonged release pharmaceutical compositions may be obtained by the methods described hereinafter.

In some embodiments pharmaceutical dosage forms comprising at least hydromorphone or a pharmaceutically acceptable salt or derivative thereof and naloxone or a pharmaceutically acceptable salt or derivative thereof are manufactured in accordance with the invention, wherein the amount of hydromorphone or a pharmaceutically acceptable salt or derivative thereof and naloxone or a pharmaceutically acceptable salt or derivative thereof released in vitro in 500 or 900 ml of Simulated Gastric Fluid, pH 1.2 using the Ph. Eur. paddle method at 100 rpm at 37° C. is:
- at 1 h: 25 to 55% by weight of the pharmaceutically active agents,
- at 2 h: 45 to 75% by weight of the pharmaceutically active agents,
- at 3 h: 55 to 85% by weight of the pharmaceutically active agents,
- at 4 h: 60 to 90% by weight of the pharmaceutically active agents,
- at 6 h: 70 to 100% by weight of the pharmaceutically active agents,
- at 8 h: more than 85% by weight of the pharmaceutically active agents,
- at 10 h: more than 90% by weight of the pharmaceutically active agents.

The pharmaceutically active agents may be an opioid agonist with hydromorphone HCl and an opioid antagonist with naloxone HCl being preferred. The prolonged release pharmaceutical composition may comprise these actives in the above indicated amounts and weight ratio of about 2:1, about 1:1, about 1:2 or about 1:3. The composition may be alcohol resistant as described hereinafter.

In further embodiments pharmaceutical dosage forms comprising at least hydromorphone or a pharmaceutically acceptable salt or derivative thereof and naloxone or a pharmaceutically acceptable salt or derivative thereof are manufactured in accordance with the invention, wherein the amount of hydromorphone or a pharmaceutically acceptable salt or derivative thereof or naloxone or a pharmaceutically acceptable salt or derivative thereof released in vitro in 500 or 900 ml of Simulated Gastric Fluid, pH 1.2 using the Ph. Eur. paddle method at 100 rpm at 37° C. is:
- at 1 h: 30 to 50% by weight of the pharmaceutically active agents,
- at 2 h: 50 to 70% by weight of the pharmaceutically active agents,
- at 3 h: 60 to 80% by weight of the pharmaceutically active agents,
- at 4 h: 65 to 85% by weight of the pharmaceutically active agents,
- at 6 h: 75 to 95% by weight of the pharmaceutically active agents,
- at 8 h: more than 90% by weight of the pharmaceutically active agents,
- at 10 h: more than 100% by weight of the pharmaceutically active agents.

The pharmaceutically active agents may preferably be an opioid agoinist hydromorphone HCl and an opioid antagonist with naloxone HCl being preferred. The prolonged release pharmaceutical composition may comprise these actives in the above indicated amounts and weight ratio of about 2:1, about 1:1, about 1:2 or about 1:3. The composition may be alcohol resistant as described hereinafter.

Prolonged release pharmaceutical compositions in accordance with the invention comprise a prolonged release matrix, which ensures prolonged release of the active ingredients. In addition prolonged release compositions may comprise e.g. a fraction of a pharmaceutically active agent in immediate release form. Such an immediate release phase, which may account for up to 30% of the overall amount of the pharmaceutically active agent being present in the composition can ensure an early onset of therapeutic efficacy.

Prolonged release pharmaceutical compositions in accordance with the invention provide for storage stability, i.e. they provide for substantially the same in vitro release rate after storage under stressed conditions.

Storage under stressed conditions in the context of the present invention means that a pharmaceutical composition is subjected to increased temperature and/or relative humidity (RH) for prolonged periods of time. For example, typical stressed conditions refer to storage over at least one, two, three, four, five, six, twelfth or eighteen months at 25° C. and 60% relative humidity (RH). Other stressed conditions refer to storage over at least one, two, three, four, five, six or twelfth months at 30° C. and 65% RH and storage over at least one, two, three, four, five or six months at 40° C. and 75% RH.

Such stressed storage conditions are used to determine whether a pharmaceutical composition has a shelf life sufficient for long time storage under conditions as they are common in patients' households without negative effects on its efficacy. Such negative effects may include that the in-vitro release rates change over time so that the efficacy of the composition is affected as different amounts of actives are released after administration. Similarly, negative effects may also result from degradation of the pharmaceutically active agents which may either decrease the overall amount of functional pharmaceutically active agent or lead to formation of toxic by-products.

If changes in the in vitro release profile or with respect to the amount of the active agents) of a pharmaceutical composition are observed after storage under stressed conditions, this may be indicative of stability problems. If such changes are not observed, this means vice versa that the pharmaceutical composition is storage stable.

The term "substantially the same release rate" refers to the situation where the in vitro release rate for a pharmaceutical composition which has been subjected to stressed conditions is compared to a reference composition. The reference composition is an identical pharmaceutical composition, which, however, has not been subjected to stressed conditions. If the in vitro release profile of the composition subjected to stressed conditions does not deviate by more than 20%, preferably by no more than 15%, more preferably by no more than 10% and even more preferably by no more than 5% from the in vitro release profile of the reference composition, the in vitro release rate is considered to be substantially the same.

Prolonged release pharmaceutical compositions with the above properties can be obtained using a method of manufacturing comprising at least the steps of:
- a) producing granules comprising at least one prolonged release material and at least one pharmaceutically active agent;
- b) optionally selecting granules of step a) of substantially uniform size;
- c) blending said granules of step a) or step b) with at least one second pharmaceutically active agent;
- d) compressing said blended granules of step c) to obtain an oral prolonged release pharmaceutical composition in the form of a tablet.

Optionally, the method may include the step of curing the compressed granules of step d).

It is to be understood that at least the compression step d) produces an oral prolonged release pharmaceutical composition in the form of a tablet, which comprises a prolonged release matrix.

The person skilled in the art is aware of different means and methods for producing granules according to step a).

In one embodiment, such granules may be produced by wet granulation. Thus, for producing granules, step a) may comprise the following steps:
aa) blending a prolonged release material optionally with at least one pharmaceutically acceptable excipient and at least one first pharmaceutically active agent,
ab) wet granulating said blend of step aa) to obtain granules, and
ac) drying said granules of step ab).

The pharmaceutically acceptable excipients may include fillers, binders, anti-tacking agents, lubricants, etc.

The filler (diluents) may include e.g. lactose, preferably anhydrous lactose, glucose or saccharose, starches, their hydrolysates, microcrystalline cellulose, cellatose, sugar alcohols such as sorbitol or mannitol, polysoluble calcium salts like calcium hydrogen phosphate, dicalcium- or tricalcium phosphate.

Lubricants can include highly dispersed silica, talcum, magnesium oxide and magnesium- or calcium stearate, sodium stearyl fumarate, fats like hydrated castor oil and glyceryl dibehenate.

Binders can include hyproxypropylmethyl cellulose(hypromellose), hydroxypropyl cellulose, hydroxyethyl cellulose, polyvinyl pyrollidone(povidone), acetic acid vinyl ester(copovidone) and carboxymethycellulose sodium.

Anti-tacking agents may include glycerol monostearate.

Wet granulation may be performed using a rotary pan-granulation or a fluidised bed granulation device.

Alternatively and/or additionally granules according to step a) may be produced comprising the steps of:
aa) blending a prolonged release material optionally with a pharmaceutically acceptable excipient and at least one first pharmaceutically active agent,
ab) optionally wet granulating said blend of step aa) to obtain granules, and
ac) extruding said wet granulation of step ab) or said mass of step ac) to obtain extruded granules,
ad) drying said granules of step ac).

The pharmaceutically acceptable material may again be fillers, binders, anti-tacking agents, lubricants etc. Additionally, the pharmaceutically acceptable material may be a spheronising agent if the extruded granules are to be spheronised afterwards. Such a spheronising agent may be microcrystalline cellulose.

Different extruder technology is available to obtain extruded granules. For example, one may use a gravity fed, ram, single screw or twin screw extruder. For twin screw extruders, one may use counter-rotating or co-rotating screws with or without paddle means.

The prolonged release material may be any material that is known to be capable of imparting prolonged release properties on the active agent when being formulated into a prolonged release matrix.

Such materials may be hydrophilic and/or hydrophobic materials such as gums, cellulose ethers, acrylic polymers, protein-derived materials etc.

Prolonged materials may also include fatty acids, fatty alcohols, glyceryl esters of fatty acids, polyethylene glycols, oils such as mineral and vegetable oils, and waxes. Fatty acids and fatty alcohols preferable are those with a $C_{10}$ to $C_{30}$ chain, preferably with a $C_{12}$ to $C_{24}$ chain and more preferably with a $C_{14}$ to $C_{20}$ chain or a $C_{16}$ to $C_{20}$ chain. Materials such as stearyl alcohol, cetostearyl alcohol, cetyl alcohol, myristyl alcohol and polyalkylene glycols may be preferred. Waxes may be selected from natural and synthetic waxes such as beeswax, carnauba wax. Oils may be mineral or vegetable oils and may include for example castor oil or hydrogenated castor oil.

The prolonged release matrix materials, which may be considered in the context of the present invention may also be selected from cellulose ethers.

The term "cellulose ethers" comprises cellulose-derived polymers derivatized with at least alkyl and/or hydroxyalkyl groups which may be hydrophilic or hydrophobic.

For example, the prolonged release matrix material may be a hydrophilic hydroxy alkyl cellulose such as a hydroxy (C1-C6) alkyl celluloses such as hydroxypropyl cellulose, hydroxypropylmethyl cellulose and particularly preferably hydroxyethyl cellulose.

Examples of hydrophobic cellulose ethers include e.g. ethyl cellulose, etc. The use of ethyl cellulose may be preferred.

A particularly suitable material for prolonged release matrix formulations in accordance with the present invention may be selected from the group of acrylic resins. Such acrylic resins may be made from (meth)acrylic acid (co) polymers.

There are various types of (meth)acrylic acid (co)polymers available which may be characterised according to the nature of their residues, such as neutral (meth)acrylic acid (co)polymers, (meth)acrylic acid (co)polymers with anionic residues or (meth)acrylic acid ester copolymers with cationic residues.

Neutral (meth)acrylic acid (co)polymers include polymers having 95 to 100% by weight of polymerised monomers having neutral residues. Monomers with neutral residues can be $C_1$-$C_4$ alkyl esters of acrylic or methacrylic acid such as methylmethacrylate, ethylmethacrylate, butylmethacrylate, methylacrylate, ethylacrylate and butylacrylate. For example, neutral (meth)acrylic acid (co)polymers may comprise 20 to 40% by weight ethylacrylate and 60 to 80% by weight methylmethacrylate. Such polymers are e.g. available under the tradename Eudragit® NE which is a copolymer of 30% by weight ethylacrylate and 70% by weight methylmethacrylate. This polymer is usually provided in the form of a 30% or 40% aqueous dispersion (Eudragit® NE 30 D, Eudragit® NE 40 D or Eudragit® NM 30 D).

(Meth)acrylic acid (co)polymers with functional anionic residues may be (meth)acrylic acid (co)polymers having 25 to 95% by weight of radically polymerised $C_1$ to $C_4$ alkyl esters of acrylic or methacrylic acid and 5 to 75% by weight of methacrylate monomers with an anionic group in the alkyl residue. $C_1$ to $C_4$ alkyl esters of acrylic or methacrylic acid are again methylmethacrylate, ethyl methacrylate, butylmethacrylate, methylacrylate, ethylacrylate and butylacrylate. A (meth)acrylate monomer with an anionic group in the alkyl residue may be for example acrylic acid and preferably methacrylic acid. Such methacrylic acid copolymers with an anionic functional group may comprise e.g. 40 to 60% by weight methacrylic acid and 60 to 40% by weight methylmethacrylate or 60 to 40% by weight ethyl acrylate. These types of polymers are available as Eudragit® L100/Eudragit® L 12.5 or Eudragit® L 100-55/Eudragit® L 30 D-55, respectively.

For example, Eudragit® L 100 is a copolymer of 50% by weight methylmethacrylate and 50% by weight methacrylic acid. It is also provided as a 12.5% solution (Eudragit® L 12.5). Eudragit® L 100-55 is a copolymer of 50% by weight ethylacrylate and 50% by weight methacrylic acid. It is also provided as a 30% dispersion (Eudragit® L 30 D-55).

(Meth)acrylic acid (co)polymers with an anionic functional group may also comprise 20 to 40% by weight methacrylic acid and 80 to 60% by weight methylmethacrylate. These types of polymers are usually available under the tradename Eudragit® S. It is also provided as a 12.5% solution (Eudragit® S 12.5). Another type of methacrylic acid copolymers with an anionic functional group is available under the tradename Eudragit® FS which typically comprises 10 to 30% by weight methylmethacrylate, 50 to 70% by weight methylacrylate and 5 to 15% by weight methacrylic acid. Thus, Eudragit®FS may be a polymer of 25% by weight methylmethacrylate, 65% by weight methylacrylate and 10% by weight methacrylic acid. It is usually provided as a 30% dispersion (Eudragit® FS 30 D).

(Meth)acrylic acid (co)polymers with functional cationic groups may be methacrylic acid copolymers with tertiary amino groups. Such polymers may comprise 30% to 80% by weight of radically polymerised $C_1$-$C_4$ alkyl esters of acrylic acid or methacrylic acid and 70 to 20% by weight methacrylate monomers with a tertiary amino group in the alkyl rest.

Suitable monomers with a functional tertiary amino group are disclosed e.g. in U.S. Pat. No. 4,705,695, column 3, line 64 to column 4, line 13. They include for example dimethylaminoethyl acrylate, 2-dimethylaminopropyl acrylate, dimethylaminopropyl methacrylate, dimethylaminobenzyl acrylate, dimethylaminobenzyl methacrylate, (3-dimethylamino-2,2-dimethyl)propyl acrylate, dimethylamino-2,2-dimethylpropylmethacrylate, (3-diethylamino-2,2-dimethyl) propyl acrylate and diethylamino-2,2-dimethylpropylmethacrylate. Particularly suitable is dimethylaminoethyl methacrylate. The amount of monomers with a tertiary amino group in the copolymer may vary between 20 to 70%, between 40 to 60%. The amount of $C_1$ to $C_4$ alkyl esters of acrylic or methacrylic acid may be within 70 to 30% by weight. $C_1$ to $C_4$ alcohol esters of acrylic or methacrylic acid include methylmethacrylate, ethylmethacrylate, butylmethacrylate, methylacrylate, ethylacrylate and butylacrylate. A common (meth)acrylic acid (co)polymer with a tertiary amino group may comprise 20 to 30% by weight methylmethacrylate, 20 to 30% by weight butylmethacrylate and 60 to 40% by weight dimethylaminoethyl methacrylate. For example the commercially available Eudragit® E 100 comprises 25% by weight methylmethacrylate, 25% by weight butylmethacrylate and 50% by weight dimethylaminoethyl methacrylate. Another common commercially available polymer Eudragit®E PO comprises copolymers of methylmethacrylate, butylmethacrylate and dimethylaminoethyl methacrylate in a ratio of 25:25:50.

Another type of (meth)acrylic acid (co)polymers with functional cationic groups are (meth)acrylic acid (co)polymers with a quaternary amino group. This type of (meth) acrylic acid (co)polymers typically comprises 50 to 70% of radically polymerised methylmethacrylate, 20 to 40% by weight of ethylacrylate and 12 to 2% by weight of 2-trimethylammoniumethyl methacrylate chloride. Such polymers are e.g. available under the tradenames Eudragit®RS or Eudragit®RL.

For example, Eudragit®RS comprises radically polymerised units of 65% by weight methylmethacrylate, 30% by weight ethylacrylate and 5% by weight 2-trimethylammoniumethyl methacrylate chloride. Eudragit®RL comprises radically polymerised units of 60% by weight methylmethacrylate, 30% by weight ethylacrylate and 10% by weight 2-trimethylamoniumethyl methacrylate chloride.

Prolonged release matrix materials which are particularly suitable for the present invention are e.g. the neutral (meth) acrylic acid (co)polymers or the (meth)acrylic acid (co) polymers with anionic functional groups. One may for example use mixtures of these types of polymers.

For example, one may use Eudragit®NE as a neutral (meth)acrylic acid (co)polymer and Eudragit®RSPO as a (meth)acrylic acid (co)polymer with an anionic functional group. One may also use a mixture of these types of polymers.

However, one may also use a mixture of (meth)acrylic acid (co)polymers and other prolonged release matrix materials such as cellulose ethers. For example, one may use a mixture of a neutral (meth)acrylic acid (co)polymer and a hydrophobic cellulose ether. A particularly suitable example is the combination of a Eudragit®NE together with ethyl cellulose. Another prolonged release material which may be used for the present invention may be polymers such as polyethylene oxide.

As regards polyethylene oxides, particularly those polyethylene oxides with a molecular weight in the range of $1 \times 10^5$-$5 \times 10^5$ may be used.

The amount of prolonged release material in the prolonged release formulation may be between about 30 to 90% by weight, between about 25 to 85% by weight, between about 30 to 80% by weight, about 35% by weight, about 40% by weight, about 45% by weight, about 50% by weight, about 55% by weight, about 60% by weight about 65% by weight, about 70% by weight or about 75% by weight based on the weight of the formulation. The amount of prolonged release material that is incorporated into the granules can be one way of adjusting the prolonged release properties. For example, if the amount of prolonged release material is increased, the release can be further prolonged.

Further, the release can be affected by selecting the size of the pharmaceutically active agent(s). For example, milling the at least one second pharmaceutically active agent to give a size in the range of agent-loaded granules can attribute to both actives having comparable dissolution profiles.

As mentioned above, the granules which may be produced by wet granulation may be dried. The dried granules may also be mixed with the at least one pharmaceutically active agent.

Typically, drying takes place at humidity in the range of about 0.5% to about 5.0% at a temperature in the range of about 20° C. to about 60° C. and for a time in the range of about 10 min to about 1 hour.

The granules may then be optionally screened in order to select granules of substantially uniform size. Selecting granules of substantially uniform size and compressing them with at least one pharmaceutically active agent may improve the prolonged release properties of the final prolonged release pharmaceutical composition as the active and the granules are then assumed to be more uniformly distributed which may prevent irregularities in the release profile. Granules for which at least about 70%, preferably at least about 80%, more preferably at least about 90% are of about the same mean size will typically be considered as being of substantially uniform size.

Preferably, granules are selected of a mean size in the range of about 100 μm to about 2 mm, more preferably in the range of about 200 μm to about 1,4 mm. Selection may be performed using a sieve with an appropriate mesh size.

In some embodiments the granules may be milled before selecting them for their size. Milling may both increase the yield of the selection step and improve the granules' suitability for the subsequent compression step. For milling one may use for example a rotary hammer mill or top/bottom driven conical mill.

The granules are then mixed with at least one pharmaceutically active agent by blending the granules and the active(s) in suitable equipment such as a tumbling blender or convective blender.

Before blending, the pharmaceutically active agent(s) may also be milled and optionally selected to provide a substantially uniform mean size. Active(s) for which at least about 70%, preferably at least about 80% and more preferably at least about 90% are of about the same size will typically be considered as having a substantially uniform size.

Preferably, the active agent(s) will be milled and optionally be screened to be of comparable mean size or smaller than the granules.

It can be of advantage of the active agent(s) are smaller than the granules. For example, for hydromorphone hydrochloride and naloxone hydrochloride at least about 80% and preferably at least about 90% are smaller than 200 µm while for the hydromorphone hydrochloride loaded granules at least about 80% and preferably at least about 90% are smaller than about 500 µm.

For compressing the pharmaceutically active agent(s) with the granules, one may use typical tabletting equipment such as a Kilian RLE 15A rotary tablet press.

The at least one, two or more pharmaceutically active agents which are combined with the active-loaded granule can thus be provided in substantially pure form and simply be blended with the active-free granules. Further, compression may take place directly after blending with no further intermediate steps. Substantially pure form means that the active is e.g. in crystalline and/or amorphous form, but is not combined with or e.g. embedded in other typical pharmaceutically acceptable excipients such as binders, prolonged release materials, fillers, lubricants etc. Thus the pharmaceutically active agent may not be further processed before combining it with the active-loaded granule, e.g. it may not be applied together with a prolonged release coating material on the active-loaded granules or it may e.g. not be comprised within granules comprising further excipients, which would then be compressed with the active-loaded granules. In fact, after compression of the active-loaded granules with the e.g. substantially pure active agent(s) one obtains a formulation having prolonged release properties. If the prolonged release properties are sufficient, this formulation may be directly used or it may be further modified with e.g. a cosmetic coating. The formulation may be usable as a monolithic formulation such as a tablet. Depending on the size of the compressed granules, one may use the formulation in multi-particulate form. Further, the compressed granules may in some case be milled and then used in multi-particulate form.

One advantage of the present invention is that one can produce granules made from a prolonged release matrix material, which comprise at least one pharmaceutically active agent. These active agent loaded granules can then be mixed with at least a second pharmaceutically active agent of choice to obtain a prolonged release formulation. As it is assumed that a prolonged release matrix is formed upon compression, some of the disadvantages of prolonged release coating are avoided. For example, dose dumping as a consequence of rupture of a prolonged release coating or the use of alcohol when administering a dosage form can be avoided in this way.

The use of active-loaded granules for blending with substantially pure pharmaceutically active agents, which are then compressed, to provide prolonged release can be also of particular advantage with respect to certain classes and groups of pharmaceutically active agents.

For example, prolonged release matrix systems making use of acrylic polymers, hydrophobic or hydrophilic cellulose ethers such as ethyl cellulose or hydroxyethyl cellulose, or fatty alcohols, fatty acids, glyceryl esters of fatty acids, oils, waxes, or combinations thereof have been successfully used to produce prolonged release formulations of opioid agonists as well as of opioid agonist and opioid antagonist combinations. It would therefore be desirable having a basic formulation tool such as the active-loaded granules of the present invention available that can be used to provide prolonged release as such for e.g. various opioid agonist and opioid antagonist combinations. The fine-tuning of the prolonged release properties may then be achieved by e.g. adding certain excipients when compressing the granules or by further modifying the compressed granules, e.g. with a prolonged release coating. The active-loaded granules of the present invention, particularly when they make use of the afore-mentioned prolonged release materials, seem to be particularly useful for opioid agonist and antagonist combinations as they allow incorporation of a second active agent (either the opioid agonist or antagonist) by simply compressing the active-loaded granules with the substantially pure actives. In some embodiments this straightforward approach provides prolonged release formulations of opioid agonist and antagonist combination, which release both active agents with substantially the same release rate, which can be a desired property in some cases. It has been observed that e.g. in this context milling the granules and/or the active agents can be of advantage. Further, by manufacturing e.g. opioid antagonist-loaded granules and simply compressing them with different substantially pure opioid agonists, one can quickly obtain prolonged release formulations of various opioid agonist and antagonist combinations.

The in vitro release behavior of the active agent(s) can be influenced by the choice and/or the amount of the prolonged release matrix material. Further, the release can be modified by using release modifiers when preparing the granules or compressing the active(s) and the granules.

Such release modifiers may be used to tune the release which otherwise would be obtained by compressing the granules with the pharmaceutically active agent(s), e.g. to accelerate the release or to further slow it down. Such release modifiers may be hydrophilic substances such as polyethylenglycols, hydroxypropylmethlycellulose, hydroxyethylcellulose, and the like or hydrophobic substances such as oils, waxes and the like. One may also use fatty alcohols such as stearyl alcohol, cetostearylaclohol, ceytlalcohol, myristyl alcohol and the like or fatty acids such as stearic acid. Other release modifiers may include the aforementioned (meth)acrylic acid(co)polymers such as polymers of the Eudragit® RLPO type.

Release modifiers such as polymers of the Eudragit/®RLPO type or low molecular weight hydroxypropylmethlycellulose may be preferred.

When compressing granules and active(s), one may further include typical tabletting excipients as they are commonly used in the art. For example, one may use lubricants, anti-tacking agents, binders and the like. Typical examples of tabletting excipients used at this stage of the method are glyceryl monostearate, hydroxypropylmethlycellulose, talcum or magnesium stearate.

As mentioned above, prolonged release pharmaceutical dosage forms in accordance with the invention may be additionally subjected to a curing step.

The term "curing" refers to a thermal treatment under either or both increased temperature and humidity for a prolonged period of time. Typically, curing takes place at a temperature in the range of about 30° C. to about 95° C. and for a time in the range of about 20 min to about 3 hours. Curing may take place in a convection oven. Typically curing conditions may thus be treatment at about 60° C., at about 80° C. or at about 95° C. for about 1 hour at ambient humidity.

Curing may positively affect various properties of the prolonged release pharmaceutical compositions in accordance with the invention. For example, curing may enhance the storage stability of the compositions. Storage stability can be assessed by comparing the in vitro release rates of pharmaceutical compositions immediately after manufacture and after prolonged storage under stressed storage conditions. If the in vitro release profile remains substantially the same, i.e. if the in vitro release rate after prolonged storage does not deviate by more than 20%, preferably by no more than 15% or even more preferably by no more than 10%, from the in vitro release rate immediately after manufacture, compositions is considered to be storage stable. Stressed storage conditions are storage under increased temperature and humidity such as 40° C. and 75% relative humidity (r.h.) for 1, 2 or 3 months.

Further, the compositions may be harder as a consequence of curing. This may improve the physical stability, e.g. the intactness of the formulation and may improve the prolonged release characteristics as the release is less influenced by e.g. cracking of the formulation during the release process. Hardness can also be an important aspect as e.g. abuse of dosage forms comprising e.g. opioids will be more difficult, given that it is more difficult to grind the formulation and thus negatively affect the prolonged release properties. Hardness is usually tested using a Holland C50 tablet hardness tester.

The invention is now illustrated with respect to specific examples. These examples are, however, not to be construed as limiting.

EXAMPLES

Example 1

Granules of the composition as shown in Table 1 were manufactured.

TABLE 1

| | Granules | |
|---|---|---|
| Ingredient | F888/49 Amount (mg) | F888/55 Amount (mg) |
| Hydromorphone HCl | 2.0 | |
| Naloxone HCl | | 4.0 |
| Ethyl cellulose | 32.0 | 32.0 |
| Eudragit NE 40 D* | 23.0 | 23.0 |
| Lactose Anhydrous | 29.7 | 29.7 |
| Purified Water** | 11.5 | 11.5 |
| Glycerol Monostearate 40-55% | 2.3 | 2.3 |
| Hypromellose 5.2 mPas*** | 0.23 | 0.23 |
| Talc | 5.8 | 5.8 |
| Total*** | 95.0 | 97.0 |

*The amount indicated refers to the amount of solids used
**Water was removed from the granules by drying
***The amount refers to the weight of the granules without water
The amounts refer to Hydromorphone HCl and Naloxone HCl.

To obtain granules, Hypromellose 5.2 mPas was mixed with purified water until fully dissolved using a Silverson high shear mixer. Then, whilst heating to 60° C. and maintaining mixing, glycerol monostearate 40-55% was added. When the mixture reached 60° C., heating was discontinued the mixture was cooled to <54° C. with mixing being continued. Talc was added to the Eudragit NE 40 D dispersion while stirring with a Heidolph paddle stirrer until fully dispersed. Then the hypromellose/glycerol monostearate dispersion was added to the Eudragit NE 40 D/talc dispersion with paddle stirring until a homogenous mixture was obtained. Stirring was maintained.

Ethyl cellulose, lactose, and hydromorphone hydrochloride or naloxone hydrochloride were placed into an Aeromatic Fielder S2 fluid bed granulator.

The conditions for fluidised bed granulation were as follows:

Apparatus: Aeromatic-Fielder S2 fluid bed granulator
Nozzle diameter: 1.8 mm
Spraying pressure: filter chamber
Air velocity (m/s): 4-6
Inlet Air temperature (° C.): 30-40
Spray rate (g/min×kg): 30-50
Spray time (min): 120
Product temperature (° C.): 24-26

The granules were then dried in the fluidized bed granulator at <28° C. for 20-30 minutes until the moisture content was below 2% w/w. The granules were then sieved using a Demi Finex sieve shaker with a mesh size of 1 mm. Subsequently the granules were milled using a Quadro Comil 197S.

Example 2

Granules of Example 1 were pressed into tablets (see Table 2).

TABLE 2

| | Tablets | |
|---|---|---|
| Ingredient | F888/72 Amount (mg) | F888/83 Amount (mg) |
| Hydromorphone HCl Granules F888/49 | 95.0 | |
| Naloxone HCl Granules F888/55 | | 97.0 |
| Hydromorphone HCl | | 2.0 |
| Naloxone HCl | 4.0 | |
| Magnesium stearate | 1.0 | 1.0 |
| Total | 100 | 100 |

The amounts refer to Hydromorphone HCl and Naloxone HCl.

For obtaining the tablets, granules of Example 1 were blended with hydromorphone HCl, or naloxone HCl and magnesium stearate using an Apex cone blender. Tablets were obtained by compressing the blend using a Kilian rotary tablet press at a tablet speed of up to 50,000 tablets/hr.

Tablet F888/72 was cured in a convection oven at 60° C. for 1 h. The cured tablet was labeled F892/15.

Tablet F888/83 was cured at 60° C. for 1 h. The cured tablet was labeled F892/16.

The tablets were then analysed as regards in vitro release behavior using the Ph. European paddle method at 100 rpm in simulated gastric fluid (SGF) dissolution medium (0.1 N HCl pH 1.2). Aliquots of the dissolution media were withdrawn at the respective time points and analysed by HPLC at 220 nm.

The tablets were further evaluated with respect to their alcohol resistance. To this end in vitro release rates were determined using the Ph. European paddle method at 100 rpm in simulated gastric fluid (SGF) dissolution medium (0.1 N HCl pH 1.2) with 40% EtOH. Aliquots of the dissolution media were withdrawn at the respective time points and analysed by HPLC at 220 nm.

The results of the release rate are indicated as percentage (based on the label content of active tested) in Tables 3 and 4.

TABLE 3

| | Tablets | | | |
|---|---|---|---|---|
| | F892/15 | | F892/15 | |
| | Dissolution medium | | | |
| | 0.1N HCl w 40% EtOH | | 0.1N HCl pH 1.2 | |
| Active tested | Hm | Nal | Hm | Nal |
| 0.5 h | 9 | 10 | 23 | 27 |
| 1 h | 14 | 14 | 32 | 37 |
| 2 h | 28 | 26 | 44 | 50 |
| 3 h | n.t. | n.t. | 54 | 58 |
| 4 h | n.t. | n.t. | 61 | 65 |
| 5 h | n.t. | n.t. | 67 | 71 |
| 6 h | n.t. | n.t. | 73 | 76 |
| 7 h | n.t. | n.t. | 79 | 81 |
| 8 h | n.t. | n.t. | 82 | 84 |
| 9 h | n.t. | n.t. | 86 | 86 |
| 10 h | n.t. | n.t. | 88 | 88 |
| 11 h | n.t. | n.t. | 90 | 89 |
| 12 h | n.t. | n.t. | 91 | 90 |

Hm = hydromorphone HCl, Nal = naloxone HCl, n.t. = not tested, 0.1N HCl w 40% EtOH = 0.1N HCl pH 1.2 with 40% ethanol. The values are the average of 3 measurements.

TABLE 4

| | Tablets | | | |
|---|---|---|---|---|
| | F892/16 | | F892/16 | |
| | Dissolution medium | | | |
| | 0.1N HCl w 40% EtOH | | 0.1N HCl pH 1.2 | |
| Active tested | Hm | Nal | Hm | Nal |
| 0.5 h | 15 | 8 | 28 | 21 |
| 1 h | 20 | 13 | 37 | 30 |
| 2 h | 33 | 25 | 47 | 42 |
| 3 h | n.t. | n.t. | 55 | 51 |
| 4 h | n.t. | n.t. | 61 | 58 |
| 5 h | n.t. | n.t. | 67 | 65 |
| 6 h | n.t. | n.t. | 72 | 71 |
| 7 h | n.t. | n.t. | 77 | 76 |
| 8 h | n.t. | n.t. | 80 | 80 |
| 9 h | n.t. | n.t. | 82 | 83 |
| 10 h | n.t. | n.t. | 85 | 85 |
| 11 h | n.t. | n.t. | 86 | 87 |
| 12 h | n.t. | n.t. | 87 | 88 |

Hm = hydromorphone HCl, Nal = naloxone HCl, n.t. = not tested, 0.1N HCl w 40% EtOH = 0.1N HCl pH 1.2 with 40% ethanol, 0.1N HCl w/o 40% EtOH = 0.1N HCl pH 1.2 without 40% ethanol. The values are the average of 3 measurements.

Tablets F892/15 and F892/16 were further subjected to prolonged storage under ICH stressed conditions, namely storage at 40° C./75% RH for 1,2 or 3 months.

The tablets were then analysed as regards in vitro release behavior using the Ph. European paddle method at 100 rpm in simulated gastric fluid (SGF) dissolution medium (0.1 N HCl pH 1.2). Aliquots of the dissolution media were withdrawn at the respective time points and analysed by HPLC at 220 nm.

The results of the release rate are indicated as percentage (based on the label content of active tested) in tables 5 and 6.

TABLE 5

| | Tablets | | | | | | | |
|---|---|---|---|---|---|---|---|---|
| | F892/15 | | F892/15 | | F892/15 | | F892/15 | |
| | | | Storage conditions | | | | | |
| | Initial | | 1 month at 40 °C., 75% RH | | 2 months at 40 °C., 75% RH | | 3 months at 40 °C., 75% RH | |
| | | | Dissolution medium | | | | | |
| | 0.1N HCl pH 1.2 | | 0.1N HCl pH 1.2 | | 0.1N HCl pH 1.2 | | 0.1N HCl pH 1.2 | |
| | | | | | Active tested | | | |
| | Hm | Nal | Hm | Nal | Hm | Nal | Hm | Nal |
| 0 h | 0 | 0 | 0 | 0 | 0 | 0 | 0 | 0 |
| 0.5 h | 23 | 27 | 20 | 24 | n.d. | n.d. | 21 | 25 |
| 1 h | 32 | 37 | 27 | 31 | 30 | 31 | 32 | 37 |
| 2 h | 44 | 50 | 43 | 45 | 44 | 44 | 46 | 49 |
| 3 h | 54 | 58 | 57 | 54 | 54 | 53 | 55 | 58 |
| 4 h | 61 | 65 | 68 | 61 | 61 | 59 | 62 | 65 |
| 5 h | 67 | 71 | 72 | 66 | 66 | 63 | 67 | 69 |
| 6 h | 73 | 76 | 76 | 69 | 70 | 67 | 72 | 73 |
| 7 h | 79 | 81 | 80 | 73 | 74 | 70 | 75 | 76 |
| 8 h | 82 | 84 | 87 | 77 | 77 | 72 | 77 | 78 |
| 9 h | 85 | 86 | 90 | 79 | 79 | 73 | 80 | 81 |
| 10 h | 88 | 88 | 93 | 80 | 80 | 75 | 81 | 82 |
| 11 h | 90 | 89 | 95 | 82 | 83 | 76 | 83 | 83 |
| 12 h | 91 | 90 | 97 | 84 | 83 | 77 | 84 | 85 |

Hm = hydromorphone HCl, Nal = naloxone HCl, n.t. = not tested, 0.1N HCl w 40% EtOH = 0.1N HCl pH 1.2 with 40% ethanol, N.d. = not determined, The values are the average of 3 measurements.

TABLE 6

| | Tablets | | | | | | | |
|---|---|---|---|---|---|---|---|---|
| | F892/15 | | F892/15 | | F892/15 | | F892/15 | |
| | | | Storage conditions | | | | | |
| | Initial | | 1 month at 40 °C., 75% RH | | 2 months at 40 °C., 75% RH | | 3 months at 40 °C., 75% RH | |
| | | | Dissolution medium | | | | | |
| | 0.1N HCl pH 1.2 | | 0.1N HCl pH 1.2 | | 0.1N HCl pH 1.2 | | 0.1N HCl pH 1.2 | |
| | | | | | Active tested | | | |
| | Hm | Nal | Hm | Nal | Hm | Nal | Hm | Nal |
| 0 h | 0 | 0 | 0 | 0 | 0 | 0 | 0 | 0 |
| 0.5 h | 28 | 21 | 27 | 21 | n.d. | n.d. | 28 | 19 |
| 1 h | 37 | 30 | 34 | 29 | 33 | 27 | 39 | 28 |
| 2 h | 47 | 42 | 47 | 40 | 45 | 40 | 53 | 41 |
| 3 h | 55 | 51 | 50 | 45 | 52 | 48 | 61 | 49 |
| 4 h | 61 | 58 | 63 | 55 | 58 | 54 | 67 | 56 |
| 5 h | 67 | 65 | 67 | 60 | 61 | 59 | 71 | 60 |
| 6 h | 72 | 71 | 70 | 64 | 65 | 63 | 74 | 64 |
| 7 h | 76 | 76 | 73 | 68 | 67 | 66 | 77 | 66 |
| 8 h | 80 | 80 | 80 | 74 | 69 | 69 | 79 | 69 |

TABLE 6-continued

| | Tablets | | | |
|---|---|---|---|---|
| | F892/15 | F892/15 | F892/15 | F892/15 |
| | | Storage conditions | | |
| | Initial | 1 month at 40 °C., 75% RH | 2 months at 40 °C., 75% RH | 3 months at 40 °C., 75% RH |
| | | Dissolution medium | | |
| | 0.1N HCl pH 1.2 | 0.1N HCl pH 1.2 | 0.1N HCl pH 1.2 | 0.1N HCl pH 1.2 |
| | | Active tested | | |
| | Hm | Nal | Hm | Nal | Hm | Nal | Hm | Nal |
| 9 h | 82 | 83 | 83 | 77 | 70 | 71 | 81 | 72 |
| 10 h | 85 | 85 | 85 | 79 | 72 | 73 | 82 | 73 |
| 11 h | 86 | 87 | 85 | 81 | 74 | 75 | 84 | 75 |
| 12 h | 87 | 88 | 89 | 84 | 74 | 77 | 85 | 77 |

Hm = hydromorphone HCl, Nal = naloxone HCl, n.t. = not tested, 0.1N HCl w 40% EtOH = 0.1N HCl pH 1.2 with 40% ethanol, N.d. = not determined, The values are the average of 3 measurements.

Example 3

Granules of the composition as shown in Table 7 were manufactured.

TABLE 7

| | Granules | |
|---|---|---|
| Ingredient | F976/06 Amount (mg) | P965/20 Amount (mg) |
| Hydrocodone bitartrate | 20.0 | |
| Morphine Sulphate | | 20.0 |
| Ethyl cellulose | 43.50 | 43.50 |
| Eudragit NE 40 D* | 20.0 | 20.0 |
| Stearyl Alcohol | 7.00 | 7.00 |
| Purified Water** | 10.0 | 10.0 |
| Glycerol Monostearate 40-55% | 3.00 | 3.00 |
| Hypromellose 5.2 mPas*** | 0.15 | 0.15 |
| Glycerol Dibehenate (Compritol 888 ATO) | 3.00 | 3.00 |
| Talc | 3.33 | 3.33 |
| Total*** | 100.00 | 100.0 |

*The amount indicated refers to the amount of solids used
**Water was removed from the granules by drying
***The amount refers to the weight of the granules without water Granules were produced by fluid bed granulation similar to Example 1.

The granules were then dried in the fluidized bed granulator at <28° C. for 20-30 minutes until the moisture content was below 2% w/w and milled.

Such active-loaded granules may be then be combined with e.g. opioid antagonists such naloxone hydrochloride, which may presented in substantially pure form.

Some embodiments of the invention relate to:
1. Method of manufacturing an oral prolonged release pharmaceutical composition comprising at least the steps of:
   a) producing granules comprising at least one prolonged release material and at least one first pharmaceutically active agent;
   b) optionally selecting granules of step a) of substantially uniform size;
   c) blending said granules of step a) or step b) with at least one additional pharmaceutically active agent;
   d) compressing said blended granules of step c) to obtain an oral prolonged release pharmaceutical composition in the form of a tablet.
2. Method according to 1., further comprising the step of:
   e) curing said compressed granules of step d).
3. Method according to any of 1. or 2., wherein granules of step a) are milled using prior to step b) or step c).
4. Method according to any of 1. to 3., wherein granules of a mean size in the range of about 100 μm to about 2.0 mm are selected in step b).
5. Method according to any of s 2 to 4, wherein curing takes place at a temperature in the range of about 40° C. to about 100° C. and for a time in the range of about 10 min to about 3 hours.
6. Method according to any of 1. to 5., wherein step a) comprises the following steps:
   aa) blending a prolonged release matrix material optionally with a filler, a binder, an anti-tacking agent and/or a lubricant, and at least one first pharmaceutically active agent;
   ab) wet granulating said blend of step aa) to obtain granules;
   ac) drying said granules of step ab).
7. Method according to 6., wherein at least step ab) is performed by rotary pan granulation or fluidized bed granulation.
8. Method according to any of 1. to 5., wherein step a) comprises the following steps:
   aa) blending a prolonged release matrix material optionally with a spheronising agent, a filler, a binder, an anti-tacking agent and/or a lubricant, and at least one first pharmaceutically active agent;
   ab) wet granulating said blend of step aa
   ac) extruding said blend of step ab) to obtain granules;
   ad) optionally spheronising said granules of step ac);
   ae) drying said granules of step ab), ac) or step ad).
9. Method according to any of 6. to 8., wherein drying in step ac) takes place at a humidity in the range of about 0,5% to about 5% at a temperature in the range of about 20° C. to about 60° C. and for a time in the range of about 10 min to about 1 hour.
10. Method according to any of 1. to 9., wherein the prolonged release material is selected from the group comprising hydrophobic or hydrophilic polymers, protein-derived material, gums, waxes, oils, fatty acids or fatty alcohols
11. Method according to 10., wherein the polymers are selected from the group of cellulose ethers or (meth) acrylic acid (co)polymers.
12. Method according to any of 1. to 11., wherein the at least one first pharmaceutically active agent is an opioid agonist, preferably oxycodone, hydromorphone, hydrocodone, tramadol or oxymorphone or their pharmaceutically acceptable salts, hydrates and solvates thereof and wherein the at least one additional pharmaceutically active ingredient is an opioid antagonist, preferably naloxone, naltrexone or nalmephene or their pharmaceutically acceptable salts, hydrates and solvates.
13. Method according to any of s 1. to 12., wherein the at least one first pharmaceutically active agent is hydromorphone HCl and wherein the at least one additional pharmaceutically active ingredient is naloxone HCl.
14. Method according to any of 1. to 13., wherein the obtained dosage form releases the pharmaceutically active agent(s) with the following in vitro release when measured using the Ph. Eur. paddle method in 500 or 1000 ml of Simulated Gastric Fluid, pH 1.2 at 100 rpm at 37° C. is:
- at 0.5 h: 10 to 50% by weight of the pharmaceutically active agents,
- at 1 h: 20 to 60% by weight of the pharmaceutically active agents,
- at 2 h: 30 to 70% by weight of the pharmaceutically active agents,
- at 3 h: 40 to 80% by weight of the pharmaceutically active agents,
- at 4 h: 50 to 90% by weight of the pharmaceutically active agents,
- at 5 h: 55 to 95% by weight of the pharmaceutically active agents,
- at 6 h: 60 to 100% by weight of the pharmaceutically active agents,
- at 8 h: 70 to 100% by weight of the pharmaceutically active agents,
- at 12 h: 80 to 100% by weight of the pharmaceutically active agents.

15. Method according to any of 1. to 14., wherein the obtained dosage form releases the pharmaceutically active agent(s) with the following in vitro release when measured using the Ph. Eur. paddle method in 500 or 1000 ml of Simulated Gastric Fluid, pH 1.2 at 100 rpm at 37° C. is:
- at 0.5 h: 20 to 40% by weight of the pharmaceutically active agents,
- at 1 h: 25 to 45% by weight of the pharmaceutically active agents,
- at 2 h: 35 to 55% by weight of the pharmaceutically active agents,
- at 3 h: 45 to 65% by weight of the pharmaceutically active agents,
- at 4 h: 55 to 75% by weight of the pharmaceutically active agents,
- at 5 h: 60 to 80% by weight of the pharmaceutically active agents,
- at 6 h: 65 to 85% by weight of the pharmaceutically active agents,
- at 8 h: 75 to 95% by weight of the pharmaceutically active agents,
- at 12 h: 85 to 100% by weight of the pharmaceutically active agents.

16. Method according to any of 1. to 15., wherein the ratio of the amount of the at least one first pharmaceutically active agent released after 0.5, 1 or 2 hours of in vitro dissolution of the dosage form in 500 or 1000 ml of Simulated Gastric Fluid, pH 1.2 with up to 40% ethanol using the Ph. Eur. paddle method at 100 rpm at 37° C. compared to the amount of the at least one first pharmaceutically active agent released after 0.5, 1 or 2 hours of in vitro dissolution of the dosage form in 500 or 1000 ml of Simulated Gastric Fluid, pH 1.2 with 0% ethanol using the Ph. Eur. paddle method at 100 rpm at 37° C. is about 2:1 or less, about 1.5:1 or less, about 1:1 or less, about 1:1.2 or less, about 1:1.4 or less, about 1:1.6 or less, about 1:1.8 or less, about 1:2 or less, about 1:2.5 or less about 1:3 or less or about 1:5 or less.

17. Method according to any of 1. to 16., wherein the ratio of the amount of the at least one first pharmaceutically active agent released after 0.5, 1 or 2 hours of in vitro dissolution of the dosage form in 500 or 1000 ml of Simulated Gastric Fluid pH 1.2 with up to 40% ethanol using the Ph. Eur. paddle method at 100 rpm at 37° C. compared to the amount of the at least one pharmaceutically active agent released after 0.5, 1 or 2 hours in vitro dissolution of the dosage form in 500 or 1000 ml of Simulated Gastric Fluid pH 1.2 with 0% ethanol using the Ph. Eur. paddle method at 100 rpm at 37° C. is about 2:1 or less, about 1.5:1 or less, about 1:1 or less, about 1:1.2 or less, about 1:1.4 or less, about 1:1.6 or less, about 1:1.8 or less, about 1:2 or less, about 1:2.5 or less about 1:3 or less or about 1:5 or less, and wherein the ratio of the amount of the at least one additional pharmaceutically active agent released after 1 hour of in vitro dissolution of the dosage form in 500 or 1000 ml of Simulated Gastric Fluid pH 1.2 with up to 40% ethanol using the Ph. Eur. paddle method at 100 rpm at 37° C. compared to the amount of the at least one additional pharmaceutically active agent released after 0.5, 1 or 2 hours in vitro dissolution of the dosage form in 500 or 1000 ml of Simulated Gastric Fluid with 0% ethanol using the Ph. Eur. paddle method at 100 rpm at 37° C. is about 2:1 or less, about 1.5:1 or less, about 1:1 or less, about 1:1.2 or less, about 1:1.4 or less, about 1:1.6 or less, about 1:1.8 or less, about 1:2 or less, about 1:2.5 or less about 1:3 or less or about 1:5 or less.

18. Oral prolonged release pharmaceutical composition obtainable by the method of any of s 1 to 16.

The invention claimed is:

1. A method of manufacturing an oral prolonged release pharmaceutical composition comprising:
    (a) blending
        (1) granules prepared such that they comprise a prolonged release matrix material formed as a prolonged release matrix containing a first pharmaceutically active agent, with
        (2) an additional pharmaceutically active agent that is uncombined with prolonged release materials; and
    (b) compressing said blended granules of step (a);
    to obtain an oral prolonged release pharmaceutical composition as compressed granules;
    wherein the oral prolonged release pharmaceutical composition releases in vitro ≤75% by weight of each of the first pharmaceutically active agent and the additional pharmaceutically active agent at 45 min;
    the prolonged release matrix material in the granules of (1) comprises a cellulose ether, a (meth)acrylic acid (co)polymer, or a combination thereof in an amount between about 30% and about 90% by weight of the granules;
    the ratio of the first pharmaceutically active agent to the additional pharmaceutically active agent is from about 2:1 to about 1:2; and
    wherein the first pharmaceutically active agent is an opioid agonist and the additional pharmaceutically active agent is an opioid antagonist.

2. The method according to claim 1, further comprising curing said compressed granules of step (b).

3. The method according to claim 1, wherein the granules blended in step (a) are milled prior to step (a).

4. The method according to claim 1, wherein the granules blended in step (a) are of a mean size in the range of about 100 μm to about 2.0 mm.

5. The method according to claim 1, wherein step (b) takes place directly after step (a) with no intermediate steps.

6. The method according to claim 2, wherein curing takes place at a temperature in the range of about 40° C. to about 100° C. and for a time in the range of about 10 min to about 3 hours.

7. The method according to claim 1, wherein
the opioid agonist is selected from the group consisting of codeine, morphine, oxycodone, hydromorphone, hydrocodone, tramadol, oxymorphone, and pharmaceutically acceptable salts, hydrates and solvates of any of the foregoing, and
the opioid antagonist is selected from the group consisting of naloxone, naltrexone, nalmephene, and pharmaceutically acceptable salts, hydrates and solvates of any of the foregoing.

8. The method according to claim 7, wherein
the opioid agonist is oxycodone HCl, hydrocodone HCl, hydromorphone HCl, or oxymorphone HCl, and
the opioid antagonist is naloxone HCl.

9. The method according to claim 1, wherein the oral prolonged release pharmaceutical composition releases the pharmaceutically active agents with the following in vitro release when measured using the Ph. Eur. paddle method in 500 or 1000 ml of Simulated Gastric Fluid, pH 1.2 at 100 rpm at 37° C.:
at 0.5 h: 10 to 50% by weight of the pharmaceutically active agents,
at 1 h: 20 to 60% by weight of the pharmaceutically active agents,
at 2 h: 30 to 70% by weight of the pharmaceutically active agents,
at 3 h: 40 to 80% by weight of the pharmaceutically active agents,
at 4 h: 50 to 90% by weight of the pharmaceutically active agents,
at 5 h: 55 to 95% by weight of the pharmaceutically active agents,
at 6 h: 60 to 100% by weight of the pharmaceutically active agents,
at 8 h: 70 to 100% by weight of the pharmaceutically active agents, and
at 12 h: 80 to 100% by weight of the pharmaceutically active agents.

10. The method according to claim 1, wherein the ratio of the amount of the first pharmaceutically active agent released after 0.5, 1 or 2 hours of in vitro dissolution of the dosage form in 500 or 1000 ml of Simulated Gastric Fluid, pH 1.2 with up to 40% ethanol using the Ph. Eur. paddle method at 100 rpm at 37° C. compared to the amount of the first pharmaceutically active agent released after 0.5, 1 or 2 hours of in vitro dissolution of the dosage form in 500 or 1000 ml of Simulated Gastric Fluid, pH 1.2 with 0% ethanol using the Ph. Eur. paddle method at 100 rpm at 37° C. is about 2:1 or less.

11. The method according to claim 1, wherein the oral prolonged release pharmaceutical composition obtained in step (b) is in the form of a tablet or multi-particles.

12. The method according to claim 11, wherein the oral prolonged release pharmaceutical composition obtained in step (b) is in the form of a tablet.

13. The method according to claim 1, wherein the granules blended in step (a) are produced by wet granulation.

14. The method according to claim 1, wherein the granules blended in step (a) are produced by extrusion.

15. The method according to claim 1, wherein the granules blended in step (a) are selected for substantially uniform size prior to step (a).

16. The method according to claim 10, wherein the ratio of the amount of the first pharmaceutically active agent released after 0.5, 1 or 2 hours of in vitro dissolution of the dosage form in 500 or 1000 ml of Simulated Gastric Fluid, pH 1.2 with up to 40% ethanol using the Ph. Eur. paddle method at 100 rpm at 37° C. compared to the amount of the first pharmaceutically active agent released after 0.5, 1 or 2 hours of in vitro dissolution of the dosage form in 500 or 1000 ml of Simulated Gastric Fluid, pH 1.2 with 0% ethanol using the Ph. Eur. paddle method at 100 rpm at 37° C. is about 1:1 or less.

17. The method according to claim 10, wherein the ratio of the amount of the first pharmaceutically active agent released after 0.5, 1 or 2 hours of in vitro dissolution of the dosage form in 500 or 1000 ml of Simulated Gastric Fluid, pH 1.2 with up to 40% ethanol using the Ph. Eur. paddle method at 100 rpm at 37° C. compared to the amount of the first pharmaceutically active agent released after 0.5, 1 or 2 hours of in vitro dissolution of the dosage form in 500 or 1000 ml of Simulated Gastric Fluid, pH 1.2 with 0% ethanol using the Ph. Eur. paddle method at 100 rpm at 37° C. is about 1:2 or less.

18. The method according to claim 1, wherein the opioid agonist is hydromorphone or a pharmaceutically acceptable salt thereof.

19. The method according to claim 1, wherein the opioid antagonist is naloxone or a pharmaceutically acceptable salt thereof.

20. The method according to claim 1, wherein the opioid agonist is hydromorphone or a pharmaceutically acceptable salt thereof, and the opioid antagonist is naloxone or a pharmaceutically acceptable salt thereof.

21. The method according to claim 1, wherein a prolonged release matrix is formed upon compressing in step (b).

22. The method according to claim 21, wherein the prolonged release matrix formed upon compressing in step (b) is the sole structure responsible for prolonged release of the pharmaceutically active agents.

23. The method according to claim 1, wherein the oral prolonged release pharmaceutical composition releases the pharmaceutically active agents with substantially the same release rate.

24. A method of manufacturing an oral prolonged release pharmaceutical composition comprising:
(a) blending
(1) granules prepared such that they comprise a prolonged release matrix material formed as a prolonged release matrix containing a first pharmaceutically active agent, with
(2) an additional pharmaceutically active agent that is uncombined with prolonged release materials; and
(b) compressing said blended granules of step (a);
to obtain an oral prolonged release pharmaceutical composition as compressed granules;
wherein a prolonged release matrix is formed upon compressing in step (b);
the oral prolonged release pharmaceutical composition releases in vitro ≤75% by weight of each of the first pharmaceutically active agent and the additional pharmaceutically active agent at 45 min;
the prolonged release matrix material in the granules of (1) comprises a cellulose ether, a (meth)acrylic acid (co)polymer, or a combination thereof in an amount between about 30% and about 90% by weight of the granules;
the ratio of the first pharmaceutically active agent to the additional pharmaceutically active agent is from about 2:1 to about 1:2;
the first pharmaceutically active agent is an opioid agonist and the additional pharmaceutically active agent is an opioid antagonist; and wherein the oral prolonged release pharmaceutical composition releases the pharmaceutically active agents with substantially the same release rate.

25. The method according to claim 24, wherein the opioid agonist is hydromorphone or a pharmaceutically acceptable salt thereof, and the opioid antagonist is naloxone or a pharmaceutically acceptable salt thereof.

26. The method according to claim 24, wherein the prolonged release matrix formed upon compressing in step (b) is the sole structure responsible for prolonged release of the pharmaceutically active agents.

27. The method according to claim 1, wherein the additional pharmaceutically active agent is uncombined with any pharmaceutical excipients prior to the blending of step (a).

28. The method according to claim 1, wherein the oral prolonged release pharmaceutical composition releases the pharmaceutically active agents with the following in vitro release when measured using the Ph. Eur. paddle method in 500 or 1000 ml of Simulated Gastric Fluid, pH 1.2 at 100 rpm at 37° C.:
   at 12 h: 80 to 100% by weight of the pharmaceutically active agents.

29. The method according to claim 24, wherein the additional pharmaceutically active agent is uncombined with any pharmaceutical excipients prior to the blending of step (a).

30. The method according to claim 24, wherein the oral prolonged release pharmaceutical composition releases the pharmaceutically active agents with the following in vitro release when measured using the Ph. Eur. paddle method in 500 or 1000 ml of Simulated Gastric Fluid, pH 1.2 at 100 rpm at 37° C.:
   at 12 h: 80 to 100% by weight of the pharmaceutically active agents.

* * * * *